(12) United States Patent
Van Orden et al.

(10) Patent No.: US 11,282,598 B2
(45) Date of Patent: Mar. 22, 2022

(54) STARTER KIT FOR BASAL INSULIN TITRATION

(71) Applicant: Novo Nordisk A/S, Bagsvaerd (DK)

(72) Inventors: Brad Warren Van Orden, Seattle, WA (US); Jakob Oest Wielandt, Farum (DK); Thomas Dedenroth Miller, Seattle, WA (US); Tinna Bjoerk Aradottir, Copenhagen (DK); Pete Brockmeier, Copenhagen V (DK); Henrik Bengtsson, Taastrup (DK)

(73) Assignee: Novo Nordisk A/S, Bagsvaerd (DK)

( * ) Notice: Subject to any disclaimer, the term of this patent is extended or adjusted under 35 U.S.C. 154(b) by 26 days.

(21) Appl. No.: 16/327,502

(22) PCT Filed: Aug. 24, 2017

(86) PCT No.: PCT/EP2017/071332
§ 371 (c)(1),
(2) Date: Feb. 22, 2019

(87) PCT Pub. No.: WO2018/037080
PCT Pub. Date: Mar. 1, 2018

(65) Prior Publication Data
US 2019/0180857 A1 Jun. 13, 2019

Related U.S. Application Data

(60) Provisional application No. 62/379,411, filed on Aug. 25, 2016.

(30) Foreign Application Priority Data

Sep. 15, 2016 (EP) .................................... 16188931

(51) Int. Cl.
*G16H 20/17* (2018.01)
*G16H 50/50* (2018.01)
(Continued)

(52) U.S. Cl.
CPC ........ *G16H 20/17* (2018.01); *A61M 5/31568* (2013.01); *G16H 10/60* (2018.01);
(Continued)

(58) Field of Classification Search
CPC .................................................. G06Q 50/22–24
See application file for complete search history.

(56) References Cited

U.S. PATENT DOCUMENTS 7,651,845 B2 1/2010 Doyle, III et al.
8,073,629 B2 12/2011 Kouchi et al.
(Continued)

FOREIGN PATENT DOCUMENTS

JP 2004024699 A 1/2004
JP 2006163489 A 6/2006
(Continued)

OTHER PUBLICATIONS

S.B. Kotsiantis, "Supervised Machine Learning: A Review of Classification Techniques", 2007, Informatica, 31, 249-268, all pages, http://www.informatica.si/index.php/informatica/article/viewFile/148/140 (Year: 2007).*
(Continued)

*Primary Examiner* — Jason S Tiedeman
*Assistant Examiner* — Jessica Marie Webb
(74) *Attorney, Agent, or Firm* — Wesley Nicolas

(57) ABSTRACT

Systems and methods for treating a subject are provided. A first dataset comprising timestamped autonomous glucose measurements of the subject over a first time course is obtained. A second dataset, associated with a standing insulin regimen for the subject over the first time course and comprising insulin medicament records, is also obtained. Each record comprises a timestamped injection event including an amount and type of insulin medicament injected into the subject by an insulin pen. The first and
(Continued)

second datasets serve to calculate a glycaemic risk measure and an insulin sensitivity factor of the subject during the first time course, which are used to obtain a basal titration schedule and a fasting blood glucose profile model over a subsequent second time course for the subject. The model predicts the fasting blood glucose level of the subject based upon amounts of basal insulin medicament injected into the subject.

18 Claims, 21 Drawing Sheets

(51) Int. Cl.
| | |
|---|---|
| G16H 10/60 | (2018.01) |
| G16H 50/30 | (2018.01) |
| G16H 50/20 | (2018.01) |
| G16H 40/63 | (2018.01) |
| A61M 5/168 | (2006.01) |
| A61M 5/315 | (2006.01) |
| H04H 60/82 | (2008.01) |
| C12Q 1/54 | (2006.01) |

(52) U.S. Cl.
CPC ............ *G16H 40/63* (2018.01); *G16H 50/20* (2018.01); *G16H 50/30* (2018.01); *G16H 50/50* (2018.01); *A61M 2205/3584* (2013.01); *A61M 2230/201* (2013.01)

(56) References Cited

U.S. PATENT DOCUMENTS

| | | | |
|---|---|---|---|
| 8,548,544 B2 | 10/2013 | Kircher, Jr. et al. | |
| 9,056,165 B2 | 6/2015 | Steil et al. | |
| 9,314,190 B1* | 4/2016 | Giuffrida | A61B 5/4082 |
| 9,833,184 B2* | 12/2017 | Derchak | G16H 50/20 |
| 9,904,659 B1* | 2/2018 | Stupp | G16B 40/20 |
| 10,123,749 B2 | 11/2018 | Kamimura | |
| 10,293,109 B2* | 5/2019 | Bengtsson | G16Z 99/00 |
| 10,314,974 B2 | 6/2019 | Day et al. | |
| 10,319,476 B1* | 6/2019 | LaBorde | G16H 40/67 |
| 10,565,170 B2 | 2/2020 | Walling et al. | |
| 2008/0172205 A1* | 7/2008 | Breton | A61B 5/002 |
| | | | 702/181 |
| 2008/0269585 A1* | 10/2008 | Ginsberg | G06F 19/3456 |
| | | | 600/365 |
| 2009/0006061 A1* | 1/2009 | Thukral | G16H 10/20 |
| | | | 703/11 |
| 2010/0057040 A1 | 3/2010 | Hayter | |
| 2010/0280334 A1* | 11/2010 | Carlson | G06N 20/10 |
| | | | 600/301 |
| 2011/0022553 A1 | 1/2011 | Yonezawa | |
| 2011/0152830 A1* | 6/2011 | Ruchti | G06F 19/3468 |
| | | | 604/504 |
| 2011/0275986 A1* | 11/2011 | Bashan | A61M 5/1684 |
| | | | 604/66 |
| 2011/0313395 A1* | 12/2011 | Krulevitch | A61M 5/3129 |
| | | | 604/504 |
| 2011/0313674 A1* | 12/2011 | Duke | G06F 19/00 |
| | | | 702/19 |
| 2012/0089893 A1* | 4/2012 | Bousamra | A61B 5/4833 |
| | | | 714/807 |
| 2012/0191361 A1* | 7/2012 | Kovatchev | G06F 19/00 |
| | | | 702/19 |
| 2012/0232520 A1* | 9/2012 | Sloan | G16Z 99/00 |
| | | | 604/504 |
| 2013/0030358 A1* | 1/2013 | Yodfat | A61M 5/1413 |
| | | | 604/66 |
| 2013/0158504 A1* | 6/2013 | Ruchti | A61M 5/1723 |
| | | | 604/504 |
| 2014/0107607 A1 | 4/2014 | Estes | |
| 2014/0313052 A1* | 10/2014 | Yarger | G16H 15/00 |
| | | | 340/870.02 |
| 2015/0035959 A1* | 2/2015 | Amble | G11B 27/11 |
| | | | 348/74 |
| 2015/0217053 A1 | 8/2015 | Booth et al. | |
| 2015/0217055 A1* | 8/2015 | Booth | G06F 19/3468 |
| | | | 604/504 |
| 2016/0073952 A1* | 3/2016 | Bashan | G06F 19/3468 |
| | | | 705/2 |
| 2016/0117481 A1* | 4/2016 | Booth | A61B 5/14503 |
| | | | 604/502 |
| 2016/0193410 A1 | 7/2016 | Sloan et al. | |
| 2016/0256629 A1 | 9/2016 | Grosman et al. | |
| 2016/0302671 A1* | 10/2016 | Shariff | G16H 50/50 |
| 2016/0317743 A1* | 11/2016 | Estes | G16H 20/17 |
| 2017/0049386 A1 | 2/2017 | Abraham et al. | |
| 2017/0053552 A1 | 2/2017 | Zhong et al. | |
| 2017/0132527 A1* | 5/2017 | Ahn | G06N 7/005 |
| 2017/0329917 A1 | 11/2017 | McRaith et al. | |
| 2018/0174675 A1 | 6/2018 | Roy et al. | |
| 2018/0296142 A1 | 10/2018 | Stahl | |
| 2019/0180857 A1 | 6/2019 | Van Orden et al. | |
| 2019/0237186 A1* | 8/2019 | El-Baz | G16H 30/40 |
| 2019/0272912 A1 | 9/2019 | Van Orden et al. | |

FOREIGN PATENT DOCUMENTS

| | | | |
|---|---|---|---|
| JP | 2007312923 | A | 12/2007 |
| JP | 2010502361 | A | 1/2010 |
| JP | 2010282366 | A | 12/2010 |
| JP | 2012513221 | A | 6/2012 |
| JP | 2012513626 | A | 6/2012 |
| JP | 2014109984 | A | 6/2014 |
| JP | 2017524414 | A | 8/2017 |
| JP | 2019536124 | A | 12/2019 |
| WO | 2007/116226 | A2 | 10/2007 |
| WO | 2009/075925 | A1 | 6/2009 |
| WO | 2009/146119 | A2 | 12/2009 |
| WO | 2009/146121 | A2 | 12/2009 |
| WO | 2010/089304 | A1 | 8/2010 |
| WO | 2010/098931 | A1 | 9/2010 |

OTHER PUBLICATIONS

I.S. Dhillon et al, "Information-Theoretic Co-clustering", 2003, University of Texas at Austin, all pages, http://www.cs.utexas.edu/users/inderjit/public_papers/kdd_cocluster.pdf (Year: 2003).*

Singleton, Robert P. and Weisstein, Eric W. "Reciprocal." 2015. Retrieved from MathWorld—A Wolfram Web Resource using Wayback Archive. https://mathworld.wolfram.com/Reciprocal.html. (Year: 2015).*

Kuroda, Akio et al., "Basal insulin requirement is ~30% of the Total Daily Insulin Dose in Type 1 Diabetic Patients Who Use the Insulin Pump", 2011, Diabetes Care, 35(5): 1089-1090, https://care.diabetesjournals.org/content/34/5/1089 (Year: 2011).*

(n.a.), "Moving variance—MATLAB movvar", Jul. 21, 2016, MathWorks, all pages, http://web.archive.org/web/20160721045020/https://www.mathworks.com/help/matlab/ref/movvar.html (Year: 2016).*

Finch, Tony, "Incremental calculation of weighted mean and variance", (2009), University of Cambridge Computing Service, all pages, https://fanf2.user.srcf.net/hermes/doc/antiforgery/stats.pdf (Year: 2009).*

Weisstein, Eric W. "Interquartile Range." 2015. Retrieved from MathWorld—A Wolfram Web Resource using Wayback Archive, http://mathworld.wolfram.com/InterquartileRange.html (Year: 2015).*

Weisstein, Eric W. "Division." Mar. 17, 2016. From MathWorld—A Wolfram Web Resource using Wayback Archive, http://mathworld.wolfram.com/Division.html (Year: 2016).*

Upton et al., "measure of spread", 2008, 2014 online version, Oxford University Press, all pages, https://www.oxfordreference.com/view/10.1093/acref/9780199541454.001.0001/acref-9780199541454-e-1027 (Year: 2014).*

Weisstein, Eric W. "Standard Deviation." 2015. From MathWorld—A Wolfram Web Resource using Wayback Archive. all pages. http://mathworld.wolfram.com/StandardDeviation.html (Year: 2015).*

(56) References Cited

OTHER PUBLICATIONS

Mahendran et al., "Investigation of the severity level of diabetic retinopathy using supervised classifier algorithms", 2015, Comp. & Elec. Engineering, vol. 45, pp. 312-323, all pages, https://www.sciencedirect.com/science/article/pii/S0045790615000191.*

Sigut et al., "An expert system for supervised classifier design: Application to Alzheimer diagnosis", 2007, Expert Systems with Applications, vol. 32, Issue 3, pp. 927-938, all pages, https://www.sciencedirect.com/science/article/pii/S0957417406000492.*

Mahendran et al., "Investigation of the severity level of diabetic retinopathy using supervised classifier algorithms", 2015, Comp. & Elec. Engineering, vol. 45, pp. 312-323, all pages, https://www.sciencedirect.com/science/article/pii/S0045790615000191. (Year: 2015).*

Sigut et al., "An expert system for supervised classifier design: Application to Alzheimer diagnosis", 2007, Expert Systems with Applications, vol. 32, Issue 3, pp. 927-938, all pages, https://www.sciencedirect.com/science/article/pii/S0957417406000492. (Year: 2007).*

S.B. Kotsiantis, "Supervised Machine Learning: A Review of Classification Techniques", Jul. 16, 2007, Informatica 31 (2007) 249-268, all pages. (Year: 2007).*

Liang, Yingyu. "Machine Learning Basics Lecture 7: Multiclass Classification", Spring 2016, Princeton University, all pages, https://www.cs.princeton.edu/courses/archive/spring16/cos495/slides/ML_basics_lecture7_multiclass.pdf (Year: 2016).*

Karthikeyani et al., "Comparative of Data Mining Classification Algorithm (CDMCA) in Diabetes Disease Population", 2012, Int J Computer App (0975-8887), vol. 60: No. 12, all pages. https://citeseerx.ist.psu.edu/viewdoc/download?doi=10.1.1.303.4111&rep=rep1&type=pdf (Year: 2012).*

Anonymous: "Cluster analysis—Wikipedia" Jan. 10, 2017 Retrieved from the Internet: URL:https://en.wikipedia.org/w/index.php?title=Cluster_analysis&oldid=759382754, retrieved on Aug. 1, 2017.

Anonymous: "Cluster analysis—Wikipedia", (Nov. 13, 2016), Retrieved from the Internet: URL:https://en.wikipedia.org/w/index.php?title=cluster_analysis&oldid=749256561, retrieved on Feb. 27, 2018.

Anonymous: "Learning classifier system—Wikipedia", Jan. 12, 2017, Retrieved from the Internet: URL:https://en.wikipedia.org/w/index.php?title=Learning_classifier_system&oldid=759708582, retrieved on Aug. 1, 2017.

Anonymous: "Learning classifier system—Wikipedia", (Nov. 28, 2016), Retrieved from the Internet: URL:https://en.wikipedia.org/w/index.php?title=Learning_classifier_system&oldid=751858603, retrieved on Feb. 27, 2018.

Blonde et al., "Patient-directed titration for achieving glycaemic goals using a once-daily basal insulin analogue: an assessment of two different fasting plasma glucose targets—the TITRATETM study," Diabetes, Obesity and Metabolism, 2009, vol. 11, pp. 623-631.

Augstein et al., "Q-Score: development of a new metric for continuous glucose monitoring that enables stratification of antihyperglycaemic therapies," BMC Endocrine Disorders, 2015, vol. 15, No. 1, Article 22.

Blonde L et al., "Patient-directed titration for achieving glycaemic goals using a once-daily basal insulin analogue: an assessment of two different fasting plasma glucose targets—the TITRATETM study" Diabetes, Obesity and Metabolism, 2009, vol. 11, No. 6, pp. 623-631.

Boris Kovatchev et al., "Glucose Variability: Timing, Risk Analysis, and Relationship to Hypoglycemia in Diabetes," Diabetes Care, 2016, vol. 39, No. 4, pp. 502-510.

Angela M. Allen, "The interaction of boronic acid based self-assembled monolayers as a potential glucose sensor," North Carolina State University, ProQuest Dissertations Publishing, 2004, 3175904, 113 pages.

* cited by examiner

402 — A device 250 for treatment of a subject is provided. The device comprises one or more processors 274 and a memory 290/192. The memory stores instructions that, when executed by the one or more processors, perform a method.

404 — Obtain a first dataset 206. The first dataset comprises a plurality of autonomous glucose measurements of the subject over a first time course. For each respective glucose measurement 208 in the plurality of autonomous glucose measurements, there is a glucose measurement timestamp 210 representing when the respective measurement was made.

406 — Successive measurements in the plurality of autonomous glucose measurements in the second dataset are taken from a measurement apparatus worn by the subject at an interval rate of 5 minutes or less, 3 minutes or less, or 1 minute or less.

408 — The device further comprises a wireless receiver, and the first dataset is obtained wirelessly from a glucose sensor 102 affixed to the subject.

410 — Obtain a second dataset 212 associated with a standing insulin regimen 224 for the subject over the first time course. The second dataset comprises a first plurality of insulin medicament records. Each respective insulin medicament record 214 in the first plurality of insulin medicament records comprises: (i) a respective insulin medicament injection event 216 including an amount of insulin medicament injected 218 into the subject using a respective insulin pen 104 of one or more insulin pens used by the subject, (ii) a corresponding insulin medicament injection event timestamp 220 for the respective insulin medicament injection event, and (iii) a respective type of insulin medicament 222 injected into the subject from one of (a) a basal insulin medicament and (b) a bolus insulin medicament.

— 412 (cont.)

—420

The standing insulin regimen for the subject over the first time course specifies a plurality of epochs (n) within the first time course, and a different daily total basal insulin medicament dosage for each respective epoch in the plurality of epochs. The insulin sensitivity factor (ISF) is calculated by:

$$ISF = \left(\frac{1}{\left(\frac{n!}{(n-2)!}\right)}\right) \sum_{n,\ i \neq j}^{\frac{n!}{(n-2)!}} \frac{\Delta FG_{i,j}}{\Delta U_{i,j}}$$

where i is a first index into the plurality of epochs, j is a second index into the plurality of epochs, $\Delta FG_{i,j}$ is the difference in average fasting glucose level of the subject between epoch i and epoch j, and $\Delta U_{i,j}$ is the difference in daily insulin dose size of the subject between epoch i and epoch j as determined by the standing insulin regimen or the second dataset.

— 422

Use at least the first glycaemic risk measure and the insulin sensitivity factor of the subject to obtain (i) a corresponding basal insulin medicament titration schedule 238 for a second time course for the subject, where the second time course occurs subsequent to the first time course, and (ii) a corresponding fasting blood glucose profile model 240 over the second time course for the subject based on the corresponding basal insulin medicament titration schedule. The corresponding fasting blood glucose profile model predicts the fasting blood glucose level of the subject based upon an amount of basal insulin medicament injected into the subject.

—424

Obtain a fifth dataset 322. The fifth dataset comprises auxiliary data 324 associated with the subject in the first time course. The auxiliary data comprises one or more of energy exerted by the subject, subject weight, subject age, and subject meal activity during the first time course. The fifth dataset is used in conjunction with the first glycaemic risk measure and the insulin sensitivity factor of the subject to obtain the corresponding basal insulin medicament titration schedule and the corresponding fasting blood glucose profile model over the second time course.

The using at least the first glycaemic risk measure and the insulin sensitivity factor of the subject comprises identifying a first treatment group 316 in a plurality of treatment groups. Each respective treatment group in the plurality of treatment groups is independently associated with a corresponding supervised classifier 318 in a plurality of supervised classifiers. The supervised classifier of the first treatment group is used to compute the corresponding fasting blood glucose profile model and the corresponding basal insulin medicament titration schedule for the second time course for the subject, thereby obtaining the corresponding basal insulin medicament titration schedule and the corresponding fasting blood glucose profile model.

— 428

The identifying the first treatment group in the plurality of treatment groups comprises co-clustering a vector of metrics 320 obtained from at least the first dataset and the second dataset against each treatment group in the plurality of treatment groups thereby obtaining a respective distance score against each treatment group in the plurality of treatment groups. The vector of metrics comprises the first glycaemic risk measure and the insulin sensitivity factor of the subject. The first treatment group is identified from among the plurality of treatment groups when the distance score for the first treatment group satisfies a confidence threshold.

— 430

The corresponding basal insulin medicament titration schedule has a fasting blood glucose target (FGL) 239 that is calculated as:
$$FGL = (w * ISF) + \sum_i^N c_i x_i$$
where w is a scaling weight, ISF is the insulin sensitivity factor of the subject calculated from the first and second datasets over the first time course, $c_i$ is an $i^{th}$ weighting constant applied to an $x_i^{th}$ glycaemic risk measure, where the $x_i^{th}$ glycaemic risk measure is in a plurality of glycaemic risk measures that includes the first glycaemic risk measure, i is an index between one and N, and N is a positive integer representing the number of glycaemic risk measures in the plurality of glycaemic risk measures.

STARTER KIT FOR BASAL INSULIN TITRATION

CROSS-REFERENCE TO RELATED APPLICATIONS

This application is a 35 U.S.C. § 371 National Stage application of International Application PCT/EP2017/071332 (published as WO 2018/037080), filed Aug. 24, 2017, which claims priority to European Patent Application 16188931.6, filed Sep. 15, 2016, this application further claims priority under 35 U.S.C. § 119 of U.S. Provisional Application 62/379,411, filed Aug. 25, 2016 the contents of all above-named applications are incorporated herein by reference.

TECHNICAL FIELD

The present disclosure relates generally to systems and methods for developing a robust basal insulin medicament titration schedule for a diabetes patient that minimizes the amount of glucose measurements needed while on the titration schedule.

BACKGROUND

Type 2 diabetes mellitus is characterized by progressive disruption of normal physiologic insulin secretion. In healthy individuals, basal insulin secretion by pancreatic β cells occurs continuously to maintain steady glucose levels for extended periods between meals. Also in healthy individuals, there is prandial secretion in which insulin is rapidly released in an initial first-phase spike in response to a meal, followed by prolonged insulin secretion that returns to basal levels after 2-3 hours.

Insulin is a hormone that binds to insulin receptors to lower blood glucose by facilitating cellular uptake of glucose, amino acids, and fatty acids into skeletal muscle and fat and by inhibiting the output of glucose from the liver. In normal healthy individuals, physiologic basal and prandial insulin secretions maintain euglycemia, which affects fasting plasma glucose and postprandial plasma glucose concentrations. Basal and prandial insulin secretion is impaired in Type 2 diabetes and early post-meal response is absent. To address these adverse events, subjects with Type 2 diabetes are provided with insulin medicament treatment regimens. Subjects with Type 1 diabetes are also provided with insulin medicament treatment regimens. The goal of these insulin medicament treatment regimens is to maintain a desired fasting blood glucose target level that will minimize estimated risk of hypo- and hyper-glycaemia.

Traditional insulin medicament delivery systems have included the use of pump systems that provide a frequent recurrent dosage of insulin medicament. More recently, additional types of delivery systems have been developed, such as insulin pens, which can be used to self-administer insulin medicament treatment regimens in the form of less frequent insulin medicament injections. A common approach to diabetes treatment using such delivery systems is to inject a single short acting insulin medicament (bolus) dosage in accordance with a standing insulin regimen for the subject in response to or in anticipation of a meal event using one insulin pen. In such approaches, the subject injects the short acting insulin medicament dosage shortly before or after one or more meals each day to lower glucose levels resulting from such meals. Further, the subject injects a long acting insulin medicament (basal) dosage in accordance with the standing insulin regimen, independent of meal events, to maintain glycaemic control independent of meal events.

Diabetes Study suggests the importance of stringent glycaemic control and current treatment guidelines call for early insulin treatment in type 2 diabetes patients. However, optimal initiation and titration methods for long-acting basal insulins are still being elucidated. Evidence suggests that many patients often do not have insulin doses titrated sufficiently to achieve target levels of glucose. Such patients remain on suboptimal insulin doses and fail to reach treatment targets.

What has become increasingly clear is that patient empowerment is important for motivation to reach treatment targets. Self-titration regimens facilitate empowerment of patients, allowing them to become more involved in their treatment, which can result in improved glycaemic control. See Blonde et al., 2009, "Patient-directed titration for achieving glycaemic goals using a once-daily basal insulin analogue: an assessment of two different fasting plasma glucose targets—the TITRATE™ study," Diabetes, Obesity and Metabolism 11:623-631.

It is clear that self-titration of insulin has great potential as it can enable treatment to target glucose levels and at the same time ease health care practitioner workload. However, patient self-titration introduces several safety and usability concerns that have to be addressed in a self-titration algorithm. Especially hazards relating to overdosing—if the algorithm suggests a higher dose of insulin medicament than is safe it could lead to hypoglycaemia and potentially dangerous situations.

FIG. 6 illustrates the result of a conventional titration for a subject that brings the subject towards a target HbA1c value using an increasing basal insulin dose over time in accordance with the prior art. The HbA1c level can be improved by long term control of the glucose level, i.e, by keeping the glucose level low. When a subject, such as a type II diabetic (T2) patient, starts on a basal insulin medicament, a titration from the initial safe suggestion (typically 10 U) to the optimal daily dose (typical range for type II diabetic patients is 40-70 [U/day]) that lowers the fasting blood glucose to a fasting glucose target level, is accomplished. Unfortunately, more than fifty percent of type II diabetic patients find titration difficult and are reluctant to change dose themselves between doctor visits. Moreover, doctors have little data to base their titration advice on, due to inadequate or misleading dosing and glucose data in the patient's logbook, if any. The result is that many patients do not reach their HbA1c treatment target, which leads to more frequent late stage complications.

Conventional self-titration algorithms, from where the resulting HbA1c is illustrated in FIG. 6, typically assume that the input is fasting blood glucose measurements taken pre-breakfast or at least pre-meal. If, for example, post-meal blood glucose measurements are used by mistake by the patient there is a risk that the titration algorithm could calculate a larger and potentially dangerous dose of insulin medicament.

Moreover, blood glucose measurements have an associated uncertainty. If, for example, users don't wash their hands before taking a measurement the results of such measurements can be much higher than the true blood glucose. If the blood glucose measurement uncertainties are not taken into account, the titration algorithm could calculate a larger and potentially dangerous dose of insulin medicament.

Moreover, most titration algorithms set the fasting blood glucose measured pre-breakfast as the target blood glucose level. There is, however, the risk that this blood glucose is, in fact, not the lowest blood glucose the patient experiences during the day, for instances, due to circumstances such as the dawn phenomenon.

Further, it is important that titration algorithms do not over-titrate and calculate too high of a dose of insulin medicament. This could lead to hypoglycaemia and potentially dangerous situations for the patient. It is also important that titration algorithms, in the absence of supervision of a physician, be able to recognize abnormal patterns and potential issues in the titration process. For instance, such titration algorithms should be able to recognize when the insulin measurement was taken incorrectly or not at all or that the blood glucose measurements were taken incorrectly.

Conventional self-titration algorithms are usually worked out on paper. This requires the patient to first measure blood glucose and then to use the paper to calculate the next insulin medicament dose. This approach can lead to problems if the paper is not used correctly or a wrong dose is entered. Still further, the best setup of a self-titration algorithm is somewhat dependent upon the type of insulin used to treat the patient and the application regime.

Unites States Patent Publication no 20120089893 entitled "Management Method and System for Implementation, Execution, Data Collection, and Data Analysis of a Structured Collection Procedure which runs on a Collection Device" to Roche Diagnosticts Operations, Inc. discloses structured collection protocols for optimizing the titration of insulin dosage, which thereby yield dosages of insulin which maintain biomarker levels within a desired range. In one embodiment, the titrated insulin may be basal insulin. Upon starting the structured collection, the dosage of insulin is typically the initial prescribed dosage. As described in the publication, it is contemplated that the structured collection may be used to obtain the optimized insulin value, or may be used as post-optimization to verify that the insulin dosage is still optimal. The structured collection protocols may optionally require the consideration of entry criteria before beginning collection of the biomarker data. It is further contemplated that the diabetic person, the healthcare provider, or both may determine whether the entry criteria are met. If the entry criteria are met, then the diabetic person may commence with the structured collection protocol. However, in some embodiments, it may be required for the diabetic person also to satisfy an adherence criteria before the collection of biomarkers or the administration of insulin. The adherence criteria are the procedural requirements that the diabetic person must follow when conducting the structured collection protocol. To get a proper baseline for the biomarker readings, it may be beneficial to ensure all readings are taken uniformly, i.e., at approximately the same time of day for each sampling instance. Consequently, the adherence criteria may specify that biomarker collection or insulin administration be conducted at the same time each day. The adherence criteria may also be directed to determining whether the diabetic person is taking the correct dosage of insulin. Despite the above disclosure, US20120089893 is appropriate for manually collected data and does not offer satisfactory teachings on a robust method of optimizing an insulin dose, without to a high extend relying on the user's ability to collect data when required by the collection procedure. Furthermore, US20120089893 does not offer teachings on how to guide the subject in titrating to target glucose levels.

Given these disparate characteristics of self-titration schemes and the general field of insulin titration methods, what is needed in the art are systems and methods that provide more robust, easy to use, insulin titration methods that achieve target glucose levels.

SUMMARY

The present disclosure addresses the need in the art for systems and methods for providing more robust, easy to use, insulin titration methods that achieve target glucose levels. A first dataset comprising timestamped autonomous glucose measurements of the subject over a first time course is obtained. A second dataset, associated with a standing insulin regimen for the subject over the first time course and comprising insulin medicament records, is also obtained. Each record comprises a timestamped injection event including an amount and type of insulin medicament injected into the subject by an insulin pen. The first and second datasets serve to calculate a glycaemic risk measure and an insulin sensitivity factor of the subject during the first time course, which are used to obtain a basal titration schedule and a fasting blood glucose profile model over a subsequent second time course for the subject. The model predicts the fasting blood glucose level of the subject based upon amounts of basal insulin medicament injected into the subject.

One aspect of the present disclosure provides a device for treatment of a subject. The device comprises one or more processors and a memory. The memory stores instructions that, when executed by the one or more processors, perform a method. In the method, a first dataset is obtained. The first dataset comprises a plurality of autonomous glucose measurements of the subject over a first time course, and, for each respective glucose measurement in the plurality of autonomous glucose measurements, a glucose measurement timestamp representing when the respective measurement was made. In the method a second dataset associated with a standing insulin regimen for the subject over the first time course is also obtained. The second dataset comprises a first plurality of insulin medicament records, and each respective insulin medicament record in the first plurality of insulin medicament records comprises: (i) a respective insulin medicament injection event including an amount of insulin medicament injected into the subject using a respective insulin pen of one or more insulin pens used by the subject, (ii) a corresponding insulin medicament injection event timestamp for the respective insulin medicament injection event, and (iii) a respective type of insulin medicament injected into the subject from one of (a) a basal insulin medicament and (b) a bolus insulin medicament. In the method, the first dataset and the second dataset are used to calculate a first glycaemic risk measure and an insulin sensitivity factor of the subject during the first time course.

At least the first glycaemic risk measure and the insulin sensitivity factor of the subject are then used to obtain a corresponding basal insulin medicament titration schedule for a second time course for the subject, where the second time course occurs subsequent to the first time course, and a corresponding fasting blood glucose profile model over the second time course for the subject based on the corresponding basal insulin medicament titration schedule. The corresponding fasting blood glucose profile model predicts the fasting blood glucose level of the subject based upon an amount of basal insulin medicament injected into the subject. The corresponding basal insulin medicament titration schedule is then communicated to (i) the subject, (ii) an insulin pen in the one or more insulin pens charged with delivering the basal insulin medicament to the subject in accordance with the corresponding basal insulin medicament titration schedule, and/or (iii) a health care practitioner associated with the subject.

In some embodiments, the method further comprises obtaining a third dataset representing all or a portion of the second time course. The third dataset comprises a plurality of fasting blood glucose values from the subject and, for each respective fasting glucose measurement in the plurality of fasting glucose measurements, a time of measurement. In such embodiments, the corresponding fasting blood glucose profile model is verified against the third dataset by matching fasting blood glucose values in the third dataset against fasting blood glucose levels estimated by the corresponding fasting blood glucose profile model based upon the corresponding basal insulin medicament titration schedule. When the corresponding fasting blood glucose profile model is deemed not verified, the method further comprises adjusting the corresponding fasting blood glucose profile model.

In some alternative embodiments, a third dataset is obtained that represents all or a portion of the second time course. The third dataset comprises a plurality of fasting blood glucose values from the subject and, for each respective fasting glucose measurement in the plurality of fasting glucose measurements, a time of measurement. Further, a fourth dataset that comprises a second plurality of insulin medicament records is obtained. Each respective insulin medicament record in the second plurality of medicament records comprises: (i) a respective insulin medicament injection event including an amount of insulin medicament injected into the subject using a respective insulin pen of one or more insulin pens used by the subject, (ii) a corresponding timestamp for the respective insulin medicament injection event, and (iii) a respective type of insulin medicament injected into the subject from one of (a) the basal insulin medicament and (b) the bolus insulin medicament. In such embodiments, the corresponding fasting blood glucose profile model is verified against the third dataset by matching fasting blood glucose values in the third dataset against fasting blood glucose levels estimated by the corresponding fasting blood glucose profile model based upon the second plurality of medicament records in the fourth dataset. When the corresponding fasting blood glucose profile model is deemed not verified, the method further comprises adjusting the corresponding fasting blood glucose profile model.

In some embodiments, the using at least the first glycaemic risk measure and the insulin sensitivity factor of the subject comprises identifying a first treatment group in a plurality of treatment groups. Each respective treatment group in the plurality of treatment groups is independently associated with a corresponding supervised classifier in a plurality of supervised classifiers. The supervised classifier of the first treatment group is used to compute the corresponding fasting blood glucose profile model and the corresponding basal insulin medicament titration schedule for the second time course for the subject, thereby obtaining the corresponding basal insulin medicament titration schedule and the corresponding fasting blood glucose profile model. In some such embodiments, the identifying the first treatment group in the plurality of treatment groups comprises co-clustering a vector of metrics, obtained from at least the first dataset and the second dataset, against each treatment group in the plurality of treatment groups thereby obtaining a respective distance score against each treatment group in the plurality of treatment groups. In such embodiments, the vector of metrics comprises the first glycaemic risk measure and the insulin sensitivity factor of the subject. The first treatment group is identified from among the plurality of treatment groups when the distance score for the first treatment group satisfies a confidence threshold.

In some embodiments, the using the first dataset and the second dataset to calculate the first glycaemic risk measure of the subject during the first time course comprises determining (i) a total glucose level variability observed across the plurality of autonomous glucose measurements, (ii) a plurality of fasting glucose levels calculated from the plurality of autonomous glucose measurements, (iii) a minimum glucose measurement observed in the plurality of autonomous glucose measurements, (iv) a maximum glucose measurement observed in the plurality of autonomous glucose measurements, (v) a rate of change in the insulin sensitivity factor calculated using the plurality of autonomous glucose measurements and the second dataset, (vi) a basal adherence score over the first time course that is computed by dividing (a) a number of insulin medicament injection events that were taken by the subject when dictated by the standing insulin regimen by (b) a total number of basal insulin medicament injection events dictated by the standing insulin regimen in the first time course, (vii) a percentage of the time glucose levels of the subject are above a first target range across the plurality of autonomous glucose measurements, (viii) a percentage of the time glucose level of the subject are below the first target range across the plurality of autonomous glucose measurements, (ix) a percentage of the time the glucose level of the subject is outside the first target range across the plurality of autonomous glucose measurements, or (x) a measure of spread of the plurality of autonomous glucose measurements.

In some embodiments, the first glycaemic risk measure comprises the fasting glucose level calculated from the plurality of autonomous glucose measurements, where the fasting glucose level is computed by computing a moving period of variance $\sigma_k^2$ across the plurality of autonomous glucose measurements, wherein:

$$\sigma_k^2 = \left( \frac{1}{M} \sum_{i=k-M}^{k} (G_i - \overline{G}) \right)^2$$

In such embodiments, $G_i$ is the $i^{th}$ autonomous glucose measurement in a portion k of the plurality of autonomous glucose measurements, M is a number of autonomous glucose measurements in the plurality of glucose measurements and represents a respective contiguous predetermined time span within the first time course, $\overline{G}$ is the mean of the autonomous glucose measurements selected from the plurality of autonomous glucose measurements, and k is within the respective contiguous predetermined time span. A fasting period in the first time course is associated with a respective contiguous predetermined time span exhibiting a minimum variance $$\min_k \sigma_k^2.$$

The fasting glucose level is then computed using autonomous glucose measurements in the plurality of autonomous glucose measurements in the fasting period. For instance, in some embodiments, the fasting glucose level is computed as (i) the minimum autonomous glucose measurement in the fasting period, (ii) a measure of central tendency across the autonomous glucose measurements in the fasting period, (iii) a range of the autonomous glucose measurement in the fasting period, (iv) an interquartile range across the autonomous glucose measurements in the fasting period, (v) a variance across the glucose measurements in the fasting period, (vi) an average squared difference across the glucose measurements in the fasting period from the mean ($\mu$) of the glucose measurements in the fasting period ($\sigma^2$) computed as:

$$\sigma^2 = \frac{\sum_{i}^{P}(m_i - \mu)^2}{P}$$

where $m_i$ is the $i^{th}$ autonomous glucose measurement in the fasting period, and P is a number of autonomous glucose measurements in the fasting period, and (vii) a standard deviation of the autonomous glucose measurements across the autonomous glucose measurements in the fasting period computed as $\sqrt{\sigma^2}$.

In some embodiments, the method further comprises obtaining a fifth dataset, where the fifth dataset comprises auxiliary data associated with the subject in the first time course, and where the auxiliary data comprises one or more of energy exerted by the subject, subject weight, subject age, and subject meal activity during the first time course. In such embodiments, the fifth dataset is used in conjunction with the first glycaemic risk measure and the insulin sensitivity factor of the subject to obtain the corresponding basal insulin medicament titration schedule and the corresponding fasting blood glucose profile model over the second time course.

In some embodiments, the standing insulin regimen for the subject over the first time course specifies a plurality of epochs (n) within the first time course, and a different daily total basal insulin medicament dosage for each respective epoch in the plurality of epochs, and the insulin sensitivity factor (ISF) is calculated by:

$$\sigma_k^2 = \left(\frac{1}{M}\sum_{i=k-M}^{k}(G_i - \overline{G})\right)^2$$

where i is a first index into the plurality of epochs, j is a second index into the plurality of epochs, $\Delta FG_{i,j}$ is the difference in average fasting glucose level of the subject between epoch i and epoch j, and $\Delta U_{i,j}$ is the difference in daily insulin dose size of the subject between epoch i and epoch j as determined by the standing insulin regimen or the second dataset.

In some embodiments, the method is repeated when the predicted fasting blood glucose profile is deemed not verified at a time in the second time course.

In some embodiments, successive measurements in the plurality of autonomous glucose measurements in the second dataset are taken at an interval rate of one day, two days, three days, four days, five days, six days, or seven days.

In some embodiments, the corresponding basal insulin medicament titration schedule has a fasting blood glucose target (FGL) that is calculated as:

$$FGL = (w * ISF) + \Sigma_i^N c_i x_i$$

where w is a scaling weight, ISF is an insulin sensitivity factor of the subject calculated from the first and second datasets over the first time course, $c_i$ is an $i^{th}$ weighting constant applied to an $x_i^{th}$ glycaemic risk measure, wherein the $x_i^{th}$ glycaemic risk measure is in a plurality of glycaemic risk measures that includes the first glycaemic risk measure, i is an index between one and N, N is a number of glycaemic risk measures in the plurality of glycaemic risk measures, and w and each $c_i$ serve the additional purpose of providing the correct dimensions to the blood glucose target. In some embodiments, successive measurements in the plurality of autonomous glucose measurements in the second dataset are taken from a measurement apparatus worn by the subject at an interval rate of 5 minutes or less, 3 minutes or less, or 1 minute or less.

15. The device of any on of claims 1-14, wherein the second data set is obtained from a respective insulin pen (104) of one or more connected insulin pens used by the subject, and wherein a corresponding insulin medicament injection event timestamp (220) is automatically generated by the respective insulin pen upon occurrence of the respective insulin medicament injection event.

In some embodiments, the one or more processors calculates a first glycaemic risk measure and an insulin sensitivity factor of the subject during the first time course, using data from a first dataset obtained from the continuous glucose monitor and a second dataset obtained from a connected insulin pen providing dose size and time stamps. The method comprises using at least the first glycaemic risk measure and the insulin sensitivity factor of the subject and a fasting blood glucose profile model, based on a generic dose-response model of a person with diabetes, establishing a relation between the first glycaemic risk measure, the insulin sensitivity factor and (i) a corresponding basal insulin medicament titration schedule for a second time course for the subject, wherein the second time course occurs subsequent to the first time course, and. The corresponding fasting blood glucose profile model over the second time course for the subject based on the corresponding basal insulin medicament titration schedule, wherein the corresponding fasting blood glucose profile model predicts the fasting blood glucose level of the subject based upon an amount of basal insulin medicament injected into the subject. Thereby the fasting blood glucose profile model, the first glyceamic risk measure and the insulin sensitivity factor can be used to obtain (i) a corresponding basal insulin medicament titration schedule for a second time course for the subject, wherein the second time course occurs subsequent to the first time course, and (ii) a corresponding fasting blood glucose profile model over the second time course for the subject based on the corresponding basal insulin medicament titration schedule, wherein the corresponding fasting blood glucose profile model predicts the fasting blood glucose level of the subject based upon an amount of basal insulin medicament injected into the subject.

In some embodiments, the fasting blood glucose profile model, based on a generic dose-response model of a person with diabetes comprises parameters established based on the data obtained during the first time course, and used to predict the insulin medicament titration schedule, and the corresponding fasting blood glucose profile, which is a profile for the fasting blood glucose level, during the second time course.

In some embodiments, the parameters are the first glycemic risk measure and the insulin sensitivity factor.

In some embodiments, the insulin medicament titration schedule during the second time course, is determined by a desired fasting blood glucose profile during the second time course.

Another aspect of the present disclosure provides a method comprising, at a computer system comprising one or more processors and a memory, using the computer system to perform a method comprising obtaining a first dataset for a subject, the first dataset comprising a plurality of autonomous glucose measurements of the subject over a first time course, and, for each respective glucose measurement in the plurality of autonomous glucose measurements, a glucose measurement timestamp representing when the respective measurement was made. The method further comprises obtaining a second dataset associated with a standing insulin regimen for the subject over the first time course. The second dataset comprises a first plurality of insulin medicament records. Each respective insulin medicament record in the first plurality of medicament records comprises: (i) a respective insulin medicament injection event including an amount of insulin medicament injected into the subject using a respective insulin pen of one or more insulin pens used by the subject, (ii) a corresponding insulin medicament injection event timestamp for the respective insulin medicament injection event, and (iii) a respective type of insulin medicament injected into the subject from one of (a) a basal insulin medicament and (b) a bolus insulin medicament. In the method, the first dataset and the second dataset are used to calculate a glycaemic risk measure and an insulin sensitivity factor of the subject during the first time course. At least the glycaemic risk measure and the insulin sensitivity factor of the subject are used to obtain (i) a corresponding basal insulin medicament titration schedule for a second time course, wherein the second time course occurs subsequent to the first time course, and (ii) a corresponding fasting blood glucose profile model over the second time course for the subject based on the corresponding basal insulin medicament titration schedule. The fasting blood glucose profile model predicts the fasting blood glucose level of the subject based upon an amount of basal insulin medicament specified by the fasting blood glucose profile model. In the method, the corresponding basal insulin medicament titration schedule is communicated to (i) the subject, (ii) an insulin pen in the one or more insulin pens charged with delivering the basal insulin medicament to the subject in accordance with the corresponding basal insulin medicament titration schedule, and/or (iii) a health care practitioner associated with the subject.

In a further aspect is provided a computer program comprising instructions that, when executed by a computer having one or more processors and a memory, perform a method comprising obtaining a first dataset for a subject, the first dataset comprising a plurality of autonomous glucose measurements of the subject over a first time course, and, for each respective glucose measurement in the plurality of autonomous glucose measurements, a glucose measurement timestamp representing when the respective measurement was made. The method further comprises obtaining a second dataset associated with a standing insulin regimen for the subject over the first time course. The second dataset comprises a first plurality of insulin medicament records. Each respective insulin medicament record in the first plurality of medicament records comprises: (i) a respective insulin medicament injection event including an amount of insulin medicament injected into the subject using a respective insulin pen of one or more insulin pens used by the subject, (ii) a corresponding insulin medicament injection event timestamp for the respective insulin medicament injection event, and (iii) a respective type of insulin medicament injected into the subject from one of (a) a basal insulin medicament and (b) a bolus insulin medicament. In the method, the first dataset and the second dataset are used to calculate a glycaemic risk measure and an insulin sensitivity factor of the subject during the first time course. At least the glycaemic risk measure and the insulin sensitivity factor of the subject are used to obtain (i) a corresponding basal insulin medicament titration schedule for a second time course, wherein the second time course occurs subsequent to the first time course, and (ii) a corresponding fasting blood glucose profile model over the second time course for the subject based on the corresponding basal insulin medicament titration schedule. The fasting blood glucose profile model predicts the fasting blood glucose level of the subject based upon an amount of basal insulin medicament specified by the fasting blood glucose profile model. In the method, the corresponding basal insulin medicament titration schedule is communicated to (i) the subject, (ii) an insulin pen in the one or more insulin pens charged with delivering the basal insulin medicament to the subject in accordance with the corresponding basal insulin medicament titration schedule, and/or (iii) a health care practitioner associated with the subject.

In a further aspect is provided a computer-readable data carrier having stored thereon the computer program as described above.

BRIEF DESCRIPTION OF THE DRAWINGS

FIGS. 4A, 4B, 4C, 4D, 4E, and 4F collectively provide a flow chart of processes and features of a device for determining a basal insulin medicament titration schedule for a subject, where optional elements of the flow chart are indicated by dashed boxes, in accordance with various embodiments of the present disclosure.

Like reference numerals refer to corresponding parts throughout the several views of the drawings.

DETAILED DESCRIPTION

Figure 1:
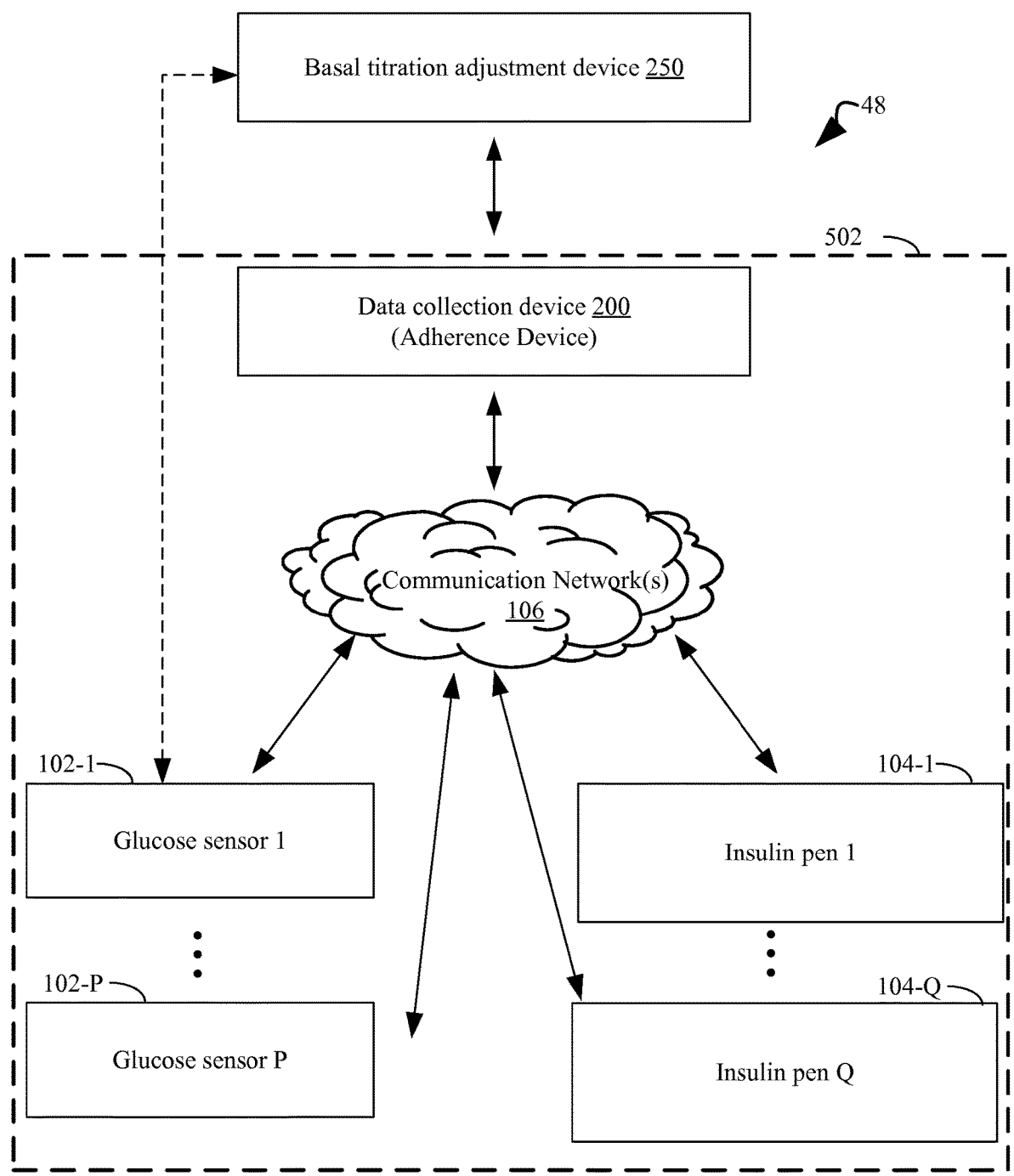
FIG. 1 illustrates an exemplary system topology that includes a basal titration adjustment device for determining a basal insulin medicament titration schedule for a subject, a data collection device for collecting patient data, one or more glucose sensors that measure glucose data from the subject, and one or more insulin pens that are used by the subject to inject insulin medicaments, where the above-identified components are interconnected, optionally through a communications network, in accordance with an embodiment of the present disclosure.
Figure 5:
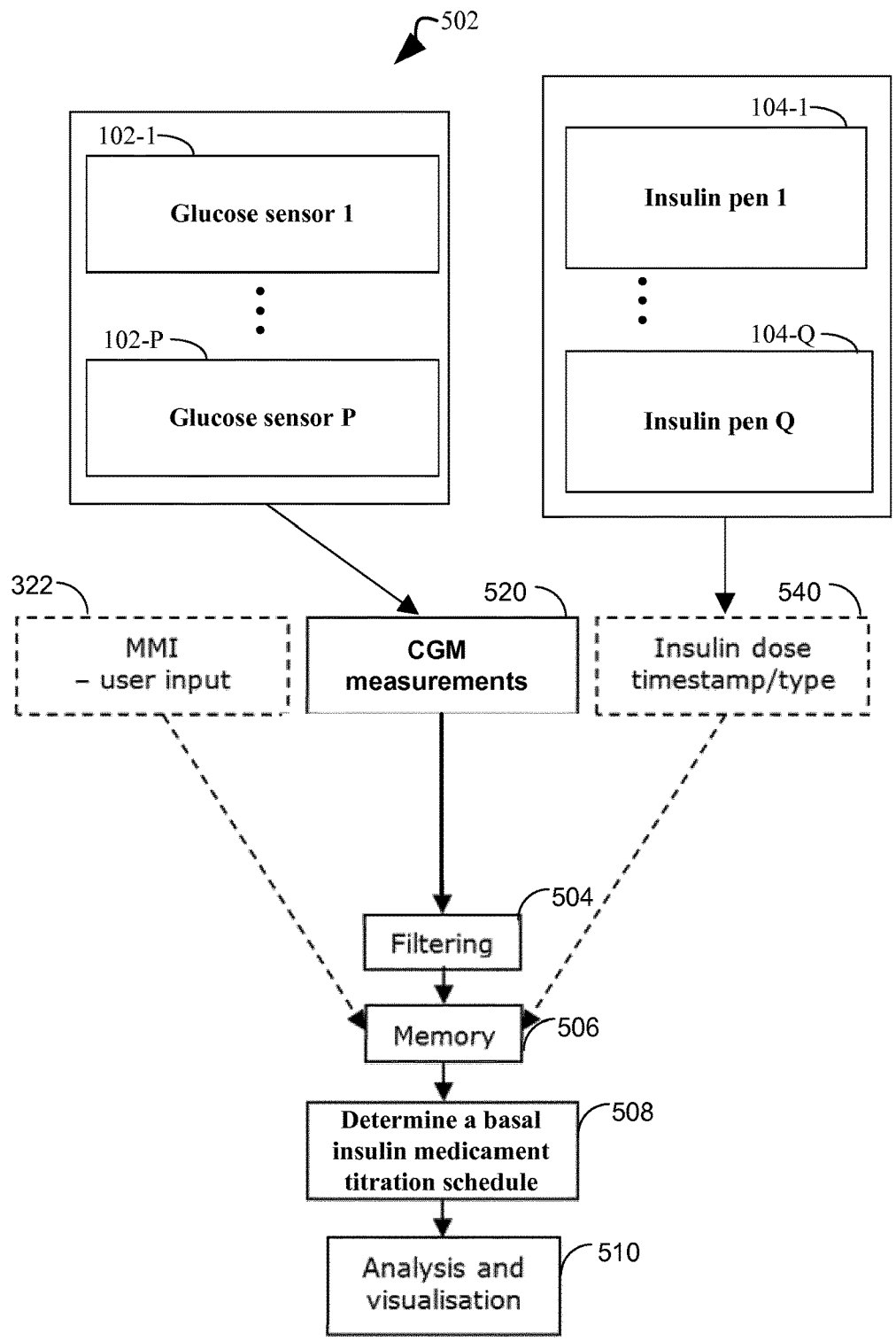
FIG. 5 illustrates an example integrated system of connected insulin pen(s), continuous glucose monitor(s), memory and a processor for determining a basal insulin medicament titration schedule for a subject in accordance with an embodiment of the present disclosure.
Figure 6:
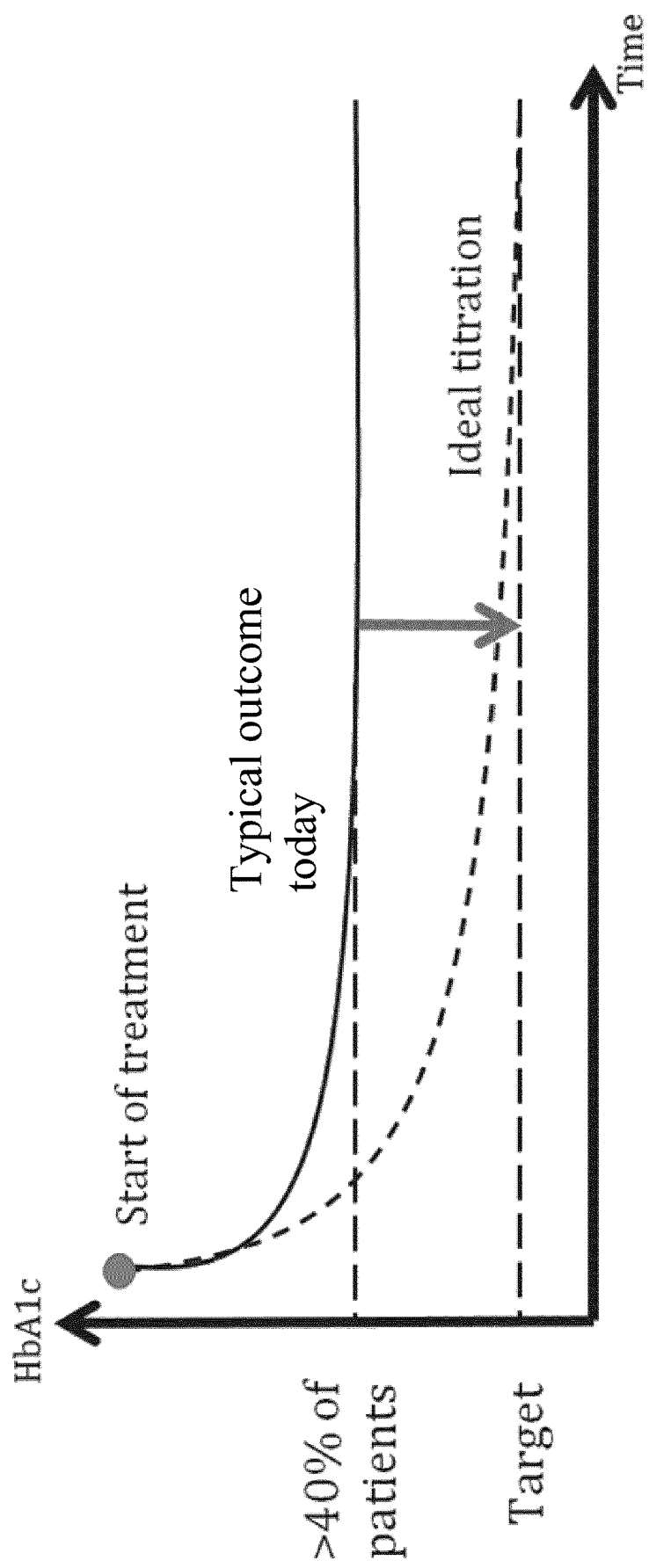
FIG. 6 illustrates a conventional titration curve for a subject that brings the subject to a target HbA1c value using insulin medicaments over time in accordance with the prior art.

The present disclosure provides systems and methods for developing a robust basal insulin medicament titration schedule for a subject. FIG. 1 illustrates an example of such an integrated system 502 in accordance with an embodiment of the present disclosure, and FIG. 5 provides more details of such a system 502. The integrated system 502 includes one or more connected insulin pens 104, one or more glucose monitors 102, memory 506, and a processor (not shown) for developing a robust basal insulin medicament titration schedule for a subject. In some embodiments, a glucose monitor 102 is a continuous glucose monitor.

With the integrated system 502, data from the one or more insulin pens 104, used to apply a standing insulin regimen 224 to the subject, is obtained 540 as a plurality of insulin medicament records. Each insulin medicament record comprises a timestamped event specifying an amount of injected insulin medicament that the subject received as part of the standing insulin medicament dosage regimen. Also, autonomous timestamped glucose measurements of the subject are obtained 520. In such embodiments, the autonomous glucose measurements are filtered 504 and stored in non-transitory memory 506. Also, in some embodiments, additional auxiliary data 322 is collected. The plurality of insulin medicament records of the subject taken over a first time course and the insulin medicament records are used to determine a basal insulin medicament titration schedule. In this way, the insulin medicament records and glucose data are analyzed and visualized in accordance with the methods of the present disclosure 510.

With the integrated system, a first dataset comprising timestamped autonomous glucose measurements of the subject over a first time course is obtained. A second dataset, associated with a standing insulin regimen for the subject over the first time course and comprising insulin medicament records, is also obtained. Each record comprises a timestamped injection event including an amount and type of insulin medicament injected into the subject by an insulin pen. In typical embodiments, at least some of the injection events are for the injection of a basal (long acting) insulin medicament. For instance, in some embodiments, some of the injection events represent injection of a basal insulin medicament while other injection events in the second dataset represent injection of a bolus (short acting) insulin medicament. The first and second datasets serve to calculate a glycaemic risk measure and an insulin sensitivity factor of the subject during the first time course, which are used to obtain a basal titration schedule and a fasting blood glucose profile model over a subsequent second time course for the subject. In some embodiments, the first time course is a two week intensive measurement period, and the second time course is the days, weeks or months after the first time course has been completed. The fasting blood glucose profile model predicts the fasting blood glucose level of the subject based upon amounts of basal insulin medicament injected into the subject. This model can be used from time to time to validate the basal titration schedule. That is, if the model cannot adequately predict the subject's glucose levels based upon the amounts of insulin medicament that subject has recently taken, the corresponding basal titration schedule is not validated and the intensive first time course is repeated to obtain a new basal titration schedule and/or the basal titration schedule is switched to a more conservative schedule with a higher glucose target and reduced insulin medicament.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein. By the term insulin pen, is meant an injection device suitable for applying discrete doses of insulin, where the injection device is adapted for logging and communicating dose related data.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Figure 2:
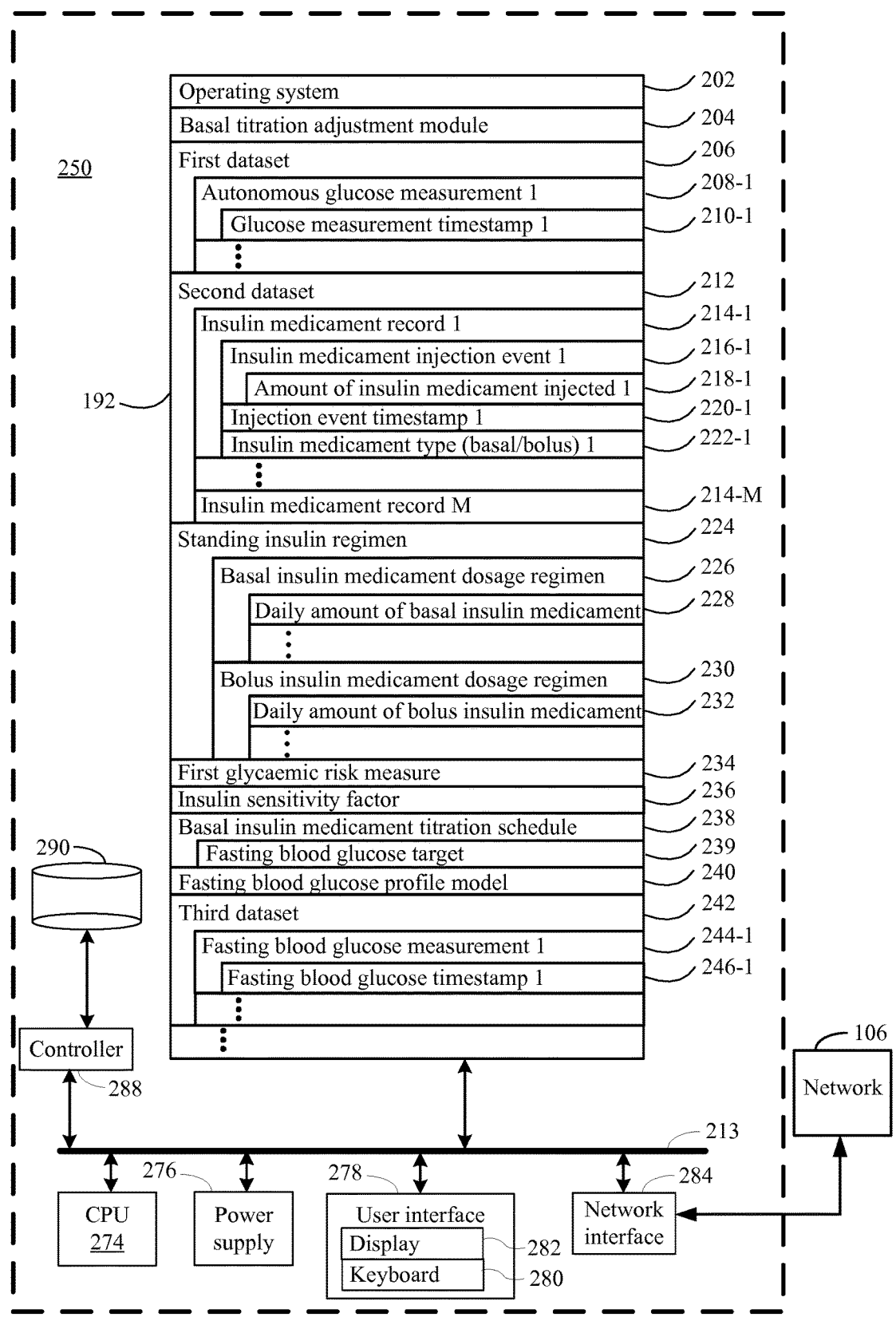
FIG. 2 illustrates a device for determining a basal insulin medicament titration schedule for a subject in accordance with an embodiment of the present disclosure.

A detailed description of a system 48 for obtaining a basal titration schedule for a subject in accordance with the present disclosure is described in conjunction with FIGS. 1 through 3. As such, FIGS. 1 through 3 collectively illustrate the topology of the system in accordance with the present disclosure. In the topology, there is a basal titration adjustment device for determining a basal insulin medicament titration schedule for a subject ("basal titration adjustment device 250") (FIGS. 1, 2, and 3), a device for data collection ("data collection device 200"), one or more glucose sensors 102 associated with the subject (FIGS. 1 and 5), and one or more insulin pens 104 for injecting insulin medicaments into the subject (FIGS. 1 and 5). Throughout the present disclosure, the data collection device 200 and the basal titration adjustment device 250 will be referenced as separate devices solely for purposes of clarity. That is, the disclosed functionality of the data collection device 200 and the disclosed functionality of the basal titration adjustment device 250 are contained in separate devices as illustrated in FIG. 1. However, it will be appreciated that, in fact, in some embodiments, the disclosed functionality of the data collection device 200 and the disclosed functionality of the basal titration adjustment device 250 are contained in a single device. In some embodiments, the disclosed functionality of the data collection device 200 and/or the disclosed functionality of the basal titration adjustment device 250 are contained in a single device and this single device is a glucose monitor 102 or an insulin pen 104.

Referring to FIG. 1, the basal titration adjustment device 250 obtains a basal titration schedule for a subject. To do this, the data collection device 200, which is in electrical communication with the basal titration adjustment device 250, receives glucose measurements originating from one or more glucose sensors 102 attached to a subject during a first time course. In some embodiments, the data collection device 200 also receives insulin medicament injection data from one or more insulin pens 104 used by the subject to inject insulin medicaments. In some embodiments, the data collection device 200 receives such data directly from the glucose sensor(s) 102 and insulin pens 104 used by the subject. For instance, in some embodiments the data collection device 200 receives this data wirelessly through radio-frequency signals. In some embodiments such signals are in accordance with an 802.11 (WiFi), Bluetooth, or ZigBee standard. In some embodiments, the data collection device 200 receives such data directly, analyzes the data, and passes the analyzed data to the basal titration adjustment device 250. In some embodiments, a glucose sensor 102 and/or insulin pen 104 includes an RFID tag and communicates to the data collection device 200 and/or the basal titration adjustment device 250 using RFID communication. In some embodiments, referring to FIGS. 3A and 3B, the data collection device 200 also obtains or receives auxiliary data 322 of the subject (e.g., from wearable physiological measurement devices, from measurement devices within the data collection device 200 such as a magnetometer or a thermostat, etc.).

In some embodiments, the data collection device 200 and/or the basal titration adjustment device 250 is not proximate to the subject and/or does not have wireless capabilities or such wireless capabilities are not used for the purpose of acquiring glucose data, insulin medicament injection data, and/or physiological measurement data. In such embodiments, a communication network 106 may be used to communicate glucose measurements from the glucose sensor 102 to the data collection device 200 and/or the basal titration adjustment device 250, insulin medicament injection data from the one or more insulin pens 104 to the data collection device 200 and/or the basal titration adjustment device 250, and/or auxiliary measurement data from one or more physiological measurement devices (not shown) to the data collection device 200 and/or the basal titration adjustment device 250.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

In some embodiments, there is a single glucose sensor 102 attached to the subject during the first time course and the data collection device 200 and/or the basal titration adjustment device 250 is part of the glucose sensor 102. That is, in some embodiments, the data collection device 200 and/or the basal titration adjustment device 250 and the glucose sensor 102 are a single device.

In some embodiments, the data collection device 200 and/or the basal titration adjustment device 250 is part of an insulin pen. That is, in some embodiments, the data collection device 200 and/or the basal titration adjustment device 250 and an insulin pen 104 are a single device.

Of course, other topologies of the system 48 are possible. For instance, rather than relying on a communications network 106, the one or more glucose sensors 102 and the one or more insulin pens 104 may wirelessly transmit information directly to the data collection device 200 and/or basal titration adjustment device 250. Further, the data collection device 200 and/or the basal titration adjustment device 250 may constitute a portable electronic device, a server computer, or in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

Referring to FIG. 2, in typical embodiments, the basal titration adjustment device 250 comprises one or more computers. For purposes of illustration in FIG. 2, the basal titration adjustment device 250 is represented as a single computer that includes all of the functionality for obtaining a basal titration schedule for a subject. However, the disclosure is not so limited. In some embodiments, the functionality for obtaining a basal titration schedule for a subject is spread across any number of networked computers and/or resides on each of several networked computers and/or is hosted on one or more virtual machines at a remote location accessible across the communications network 106. One of skill in the art will appreciate that any of a wide array of different computer topologies are used for the application and all such topologies are within the scope of the present disclosure.

Turning to FIG. 2 with the foregoing in mind, an exemplary basal titration adjustment device 250 for obtaining a basal titration schedule for a subject comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the basal titration adjustment device 250 but that can be electronically accessed by the basal titration adjustment device 250 over an Internet, intranet, or other form of network or electronic cable (illustrated as element 106 in FIG. 2) using network interface 284.

In some embodiments, the memory 192 of the basal titration adjustment device 250 for obtaining a basal titration schedule for a subject stores:

- an operating system 202 that includes procedures for handling various basic system services;
- a basal titration adjustment module 204;
- a first dataset 206, the first dataset representing a first time course and comprising a plurality of autonomous glucose measurements of the subject over the first time course, and for each respective autonomous glucose measurement 208 in the plurality of glucose measurements, a glucose measurement timestamp 210 representing when the respective glucose measurement was made;
- a second dataset 212 comprising a first plurality of insulin medicament records during the first time course, with each respective insulin medicament record 214 in the first plurality of insulin medicament records comprising: (i) a respective insulin medicament injection event 216 including an amount of insulin medicament injected 218 into the subject using a respective insulin pen 104 of one or more insulin pens used by the subject, (ii) a corresponding insulin medicament injection event timestamp 220 for the respective insulin medicament injection event, and (iii) a respective type of insulin medicament 222 injected into the subject from one of (a) a basal insulin medicament and (b) a bolus insulin medicament;
- a standing insulin regimen 224 for the subject, the standing insulin regimen comprising a basal insulin medicament dosage regimen 226 with a daily (or other recurrent period such as 12 hours, etc.) amount of basal (long acting) insulin medicament 228 specified, and further comprising a bolus (short acting) insulin medicament dosage regimen 230 with a daily (or other recurrent period, such as per meal or per meal type or per 12 hours, etc.) amount of bolus insulin medicament 232 specified;
- a first glycaemic risk measure 234 computed for a subject over a first time course;
- an insulin sensitivity factor 236 computed for a subject over a first time course;
- a basal insulin medicament titration schedule 238 for a second time course following the first time course that is computed basal titration adjustment module 204, the basal insulin medicament titration schedule optionally including a fasting blood glucose target 239;
- a fasting blood glucose profile model 240 for the second time course following the first time course that is computed by the basal titration adjustment module 204; and
- an optional third dataset 242 that comprises a plurality of fasting blood glucose measurements taken (either autonomously or manually) during the second time course, with each respective fasting blood glucose measurement 244 having an associated fasting blood glucose timestamp 246 that indicates when the respective fasting blood glucose measurement was made.

In some embodiments, the basal titration adjustment module 204 is accessible within any browser (phone, tablet, laptop/desktop). In some embodiments, the basal titration adjustment module 204 runs on native device frameworks, and is available for download onto the basal titration adjustment device 250 running an operating system 202 such as Android or iOS.

In some implementations, one or more of the above identified data elements or modules of the basal titration adjustment device 250 for obtaining a basal insulin medicament titration schedule for a subject are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments, the memory 192 and/or 290 stores additional modules and data structures not described above.

In some embodiments, a basal titration adjustment device 250 for obtaining a basal insulin medicament titration schedule for a subject is a smart phone (e.g., an iPHONE), laptop, tablet computer, desktop computer, or other form of electronic device (e.g., a gaming console). In some embodiments, the basal titration adjustment device 250 is not mobile. In some embodiments, the basal titration adjustment device 250 is mobile.

FIG. 3 provides a further description of a specific embodiment of a basal titration adjustment device 250 in accordance with the instant disclosure.

The basal titration adjustment device 250 illustrated in FIG. 3 has one or more processing units (CPU's) 274, peripherals interface 370, memory controller 368, a network or other communications interface 284, a memory 192 (e.g., random access memory), a user interface 278, the user interface 278 including a display 282 and input 280 (e.g., keyboard, keypad, touch screen), an optional accelerometer 317, an optional GPS 319, optional audio circuitry 372, an optional speaker 360, an optional microphone 362, one or more optional intensity sensors 364 for detecting intensity of contacts on the basal titration adjustment device 250 (e.g., a touch-sensitive surface such as a touch-sensitive display system 282 of the basal titration adjustment device 250), an optional input/output (I/O) subsystem 366, one or more optional optical sensors 373, one or more communication busses 213 for interconnecting the aforementioned components, and a power supply 276 for powering the aforementioned components.

In some embodiments, the input 280 is a touch-sensitive display, such as a touch-sensitive surface. In some embodiments, the user interface 278 includes one or more soft keyboard embodiments. The soft keyboard embodiments may include standard (QWERTY) and/or non-standard configurations of symbols on the displayed icons.

The basal titration adjustment device 250 illustrated in FIG. 3 optionally includes, in addition to accelerometer(s) 317, a magnetometer (not shown) and a GPS 319 (or GLONASS or other global navigation system) receiver for obtaining information concerning the location and orientation (e.g., portrait or landscape) of the basal titration adjustment device 250 and/or for determining an amount of physical exertion by the subject.

It should be appreciated that the basal titration adjustment device 250 illustrated in FIG. 3 is only one example of a multifunction device that may be used for obtaining a basal insulin medicament titration schedule 238 for a subject, and that the basal titration adjustment device 250 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 192 of the basal titration adjustment device 250 illustrated in FIG. 3 optionally includes high-speed random access memory and optionally also includes non-volatile memory, such as one or more magnetic disk storage devices, flash memory devices, or other non-volatile solid-state memory devices. Access to memory 192 by other components of the basal titration adjustment device 250, such as CPU(s) 274 is, optionally, controlled by the memory controller 368.

In some embodiments, in addition to any or all of the components (modules, data structures, etc.) in the memory 192/290 of the device 250 of FIG. 2 described above, the memory 192/290 of the basal titration adjustment device 250 illustrated in FIG. 3 optionally includes:

- a fourth dataset 206 comprising a second plurality of insulin medicament records, where each respective insulin medicament record 304 in the second plurality of medicament records comprises: (i) a respective insulin medicament injection event 306 including an amount of insulin medicament injected 308 into the subject using a respective insulin pen of one or more insulin pens used by the subject, (ii) a corresponding timestamp 310 for the respective insulin medicament injection event, where such timestamps 310 arise during the second time course, and (iii) a respective type of insulin medicament injected 312 into the subject from one of (a) the basal insulin medicament and (b) the bolus insulin medicament;
- a plurality of treatment groups 314 (FIG. 3A), each respective treatment group 316 (FIG. 3B) independently associated with a corresponding supervised classifier 318 in a plurality of supervised classifiers that is used to compute the corresponding fasting blood glucose profile model 240 and the corresponding basal insulin medicament titration schedule 238 for the second time course for the subject using a vector of metrics 320 measured from the subject during the first time course, and
- a fifth dataset 322 that comprises auxiliary data 324 associated with the subject in the form of measurements 326 made during the first time course (e.g., energy exerted by the subject, subject weight, subject age, subject meal activity).

In some embodiments, the auxiliary data 324 comprises a body temperature of the subject. In some embodiments, the auxiliary data 324 comprises a measurement of activity of the subject. In some embodiments, this auxiliary data serves as an additional input for in conjunction with the first glycaemic risk measure 234 and the insulin sensitivity factor 236 of the subject to obtain the corresponding basal insulin medicament titration schedule 238 and the corresponding fasting blood glucose profile model 240 over the second time course. In some embodiments, the optional accelerometer 317, optional GPS 319, and/or magnetometer (not shown) of the basal titration adjustment device 250 or such components optionally within the one or more glucose monitors 102 and/or the one or more insulin pens 104 is used to acquire such auxiliary data 324.

The peripherals interface 370 can be used to couple input and output peripherals of the device to CPU(s) 274 and memory 192. The one or more processors 274 run or execute various software programs and/or sets of instructions stored in memory 192/290, such as the basal titration adjustment module 204, to perform various functions for the basal titration adjustment device 250 and to process data.

In some embodiments, the peripherals interface 370, CPU(s) 274, and memory controller 368 are, optionally, implemented on a single chip. In some other embodiments, they are implemented on separate chips.

RF (radio frequency) circuitry of network interface 284 receives and sends RF signals, also called electromagnetic signals. In some embodiments, the first dataset 206, the second dataset 212, the standing insulin regimen 224, the optional third dataset 242, the optional fourth dataset 302, the optional treatment groups 314 and/or the optional fifth dataset 322 is received using this RF circuitry from one or more devices such as a glucose sensor 102 associated with a subject, an insulin pen 104 associated with the subject and/or the data collection device 200. In some embodiments, the RF circuitry 108 converts electrical signals to/from electromagnetic signals and communicates with communications networks and other communications devices, glucose sensors 102, and insulin pens 104 and/or the data collection device 200 via the electromagnetic signals. The RF circuitry 284 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. The RF circuitry 284 optionally communicates with the communication network 106. In some embodiments, the circuitry 284 does not include RF circuitry and, in fact, is connected to the network 106 through one or more hard wires (e.g., an optical cable, a coaxial cable, or the like).

In some embodiments, the audio circuitry 372, the optional speaker 360, and the optional microphone 362 provide an audio interface between the subject and the basal titration adjustment device 250. The audio circuitry 372 receives audio data from the peripherals interface 370, converts the audio data to electrical signals, and transmits the electrical signals to the speaker 360. The speaker 360 converts the electrical signals to human-audible sound waves. The audio circuitry 372 also receives electrical signals converted by the microphone 362 from sound waves. The audio circuitry 372 converts the electrical signal to audio data and transmits the audio data to peripherals interface 370 for processing. Audio data is, optionally, retrieved from and/or transmitted to the memory 192 and/or the RF circuitry 284 by the peripherals interface 370.

In some embodiments, the power supply 276 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the basal titration adjustment device 250 optionally also includes one or more optical sensors 373. The optical sensor(s) 373 optionally include charge-coupled device (CCD) or complementary metal-oxide semiconductor (CMOS) phototransistors. The optical sensor(s) 373 receive light from the environment, projected through one or more lens, and converts the light to data representing an image. The optical sensor(s) 373 optionally capture still images and/or video. In some embodiments, an optical sensor is located on the back of the basal titration adjustment device 250, opposite the display 282 on the front of the basal titration adjustment device 250, so that the input 280 is enabled for use as a viewfinder for still and/or video image acquisition. In some embodiments, another optical sensor 373 is located on the front of the basal titration adjustment device 250 so that the subject's image is obtained (e.g., to verify the health or condition of the subject, to determine the physical activity level of the subject, to help diagnose a subject's condition remotely, or to acquire visual physiological measurements 312 of the subject, etc.).

Figure 3A:
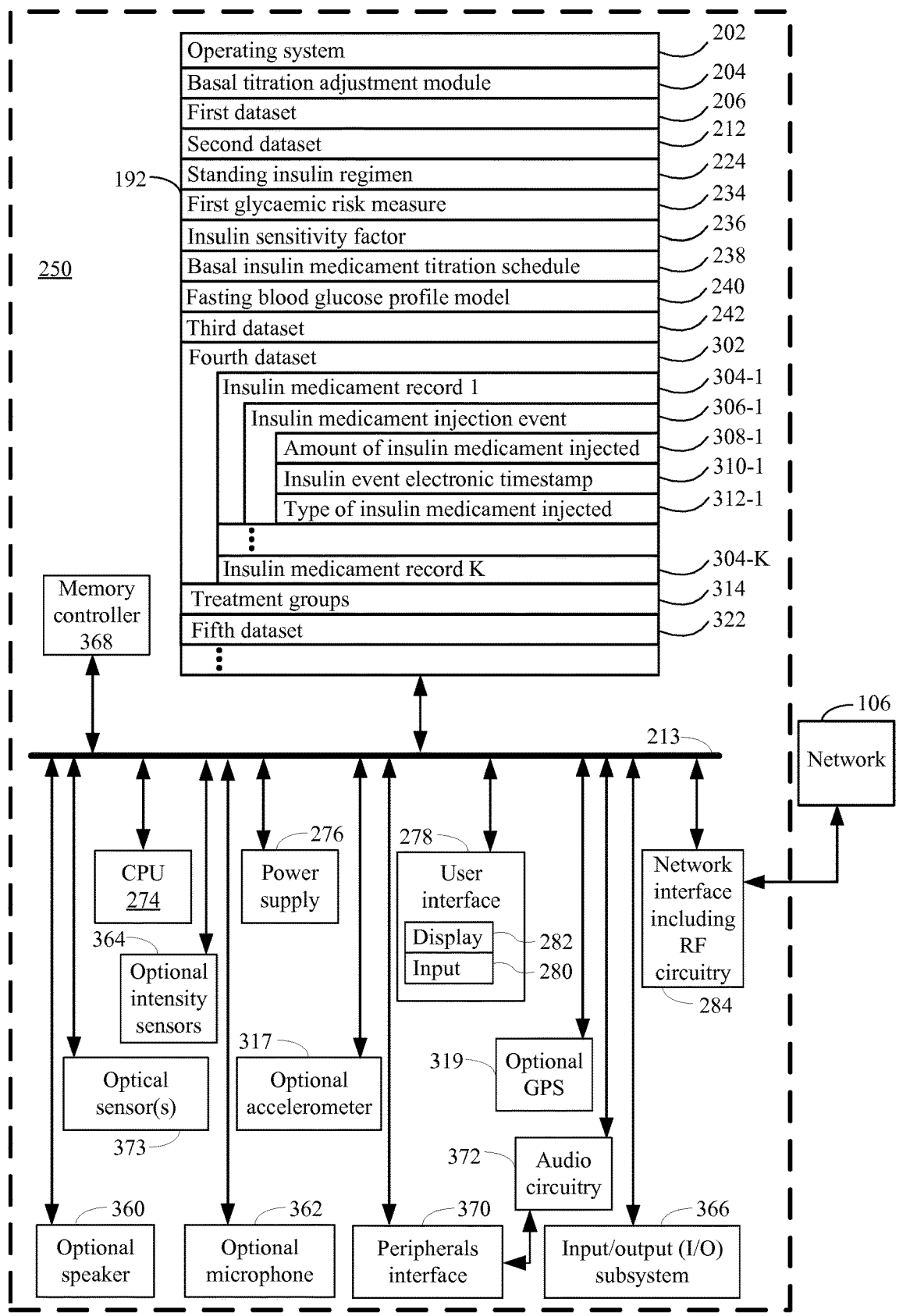
FIGS. 3A and 3B collectively illustrate a device for determining a basal insulin medicament titration schedule for a subject in accordance with another embodiment of the present disclosure.

As illustrated in FIG. 3A, a basal titration adjustment device 250 preferably comprises an operating system 202 that includes procedures for handling various basic system services. The operating system 202 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments the basal titration adjustment device 250 is a smart phone. In other embodiments, the basal titration adjustment device 250 is not a smart phone but rather is a tablet computer, desktop computer, emergency vehicle computer, or other form or wired or wireless networked device. In some embodiments, the basal titration adjustment device 250 has any or all of the circuitry, hardware components, and software components found in the basal titration adjustment device 250 depicted in FIG. 2 or 3. In the interest of brevity and clarity, only a few of the possible components of the basal titration adjustment device 250 are shown in order to better emphasize the additional software modules that are installed on the basal titration adjustment device 250.

While the system 48 disclosed in FIG. 1 can work standalone, in some embodiments it can also be linked with electronic medical records to exchange information in any way.

Now that details of a system 48 for obtaining a basal insulin medicament titration schedule for a subject have been disclosed, details regarding a flow chart of processes and features of the system, in accordance with an embodiment of the present disclosure, are disclosed with reference to FIGS. 4A through 4F. In some embodiments, such processes and features of the system are carried out by the basal titration adjustment module 204 illustrated in FIGS. 2 and 3.

Block 402. With reference to block 402 of FIG. 4A, the goal of insulin therapy in subjects with either type 1 diabetes mellitus or type 2 diabetes mellitus is to match as closely as possible normal physiologic insulin secretion to control fasting and postprandial plasma glucose. As illustrated in FIG. 2, a basal titration adjustment device 250 comprises one or more processors 274 and a memory 192/290. The memory stores instructions that, when executed by the one or more processors, perform a method.

Blocks 404-408. Referring to block 404 of FIG. 4A, in the method, a first dataset 206 is obtained. The first dataset 206 comprises a plurality of autonomous glucose measurements of the subject taken over a first time course. The glucose measurements are autonomous in the sense that the subject does not manually take the measurements. Rather, a device such a continuous glucose monitor is used to take the glucose measurement. As such, the first time course represents a data intensive period in which a substantial amount of data is acquired from the subject. Referring to block 406, in some embodiments this substantial amount of data is in the form of autonomous glucose measurements 208 in the first dataset 206 that are taken from a measurement apparatus worn by the subject at an interval rate of 5 minutes or less, 3 minutes or less, or 1 minute or less.

In some embodiments, the plurality of autonomous glucose comprises 20 autonomous glucose measurements or more, 40 autonomous glucose measurements or more, 100 autonomous glucose measurements or more, 200 autonomous glucose measurements or more, or 1000 autonomous glucose measurements or more, taken over a period of a day or more, two days or more, a week or more, two weeks or more, one month or more or over a period of less than one month, less than three weeks, or two weeks or less.

In typical embodiments, the autonomous glucose measurements are from one or more glucose sensors 102. FIG. 2 illustrates. Each such autonomous glucose measurement 208 is timestamped with a glucose measurement timestamp 210 to represent when the respective autonomous glucose measurement was made. Thus, in some embodiments, the autonomous glucose measurements are measured without human intervention. That is, the subject does not manually make the autonomous glucose measurements. In alternative less preferred embodiments of the present disclosure, the subject or a health care practitioner manually takes glucose measurements and such manual glucose measurements are used as the glucose measurements 208 in the first dataset 206.

In embodiments where autonomous glucose measurements are used in the first dataset 206, devices such as the Dexcom G5® Continuous Glucose Monitoring (CGM) by Dexcom (or G6 when launched), which provides real-time glucose readings every five minutes. Another alernative is the FREESTYLE LIBRE CGM by ABBOTT ("LIBRE") may serve as the glucose sensor 102 in order to make the plurality of autonomous glucose measurements of a subject. The LIBRE allows calibration-free glucose measurements with an on-skin coin-sized sensor, which can send up to eight hours of data to a reader device (e.g., the data collection device 200 and/or the basal titration adjustment device 250) via near field communications, when brought close together.

The LIBRE can be worn for fourteen days in all daily life activities. In some embodiments, the autonomous glucose measurements 208 are taken from the subject at an interval rate of 5 minutes or less, 3 minutes or less, or 1 minute or less, over a time period (first time course) of a day or more, two days or more, a week or more, or two weeks or more. In some embodiments, the glucose measurements 218 are autonomously taken (e.g., without human effort, without human intervention, etc.). Referring to block 408 of FIG. 4A, in some embodiments the basal titration adjustment device 250 further comprises a wireless receiver and the first dataset 206 is obtained wirelessly from a glucose sensor 102 affixed to the subject (e.g., in accordance with an 802.11, Bluetooth, or ZigBee standard).

Block 410. Referring to block 410 of FIG. 4A, in the method a second dataset 212 associated with a standing insulin regimen 224 for the subject over the first time course is also obtained. The second dataset comprises a first plurality of insulin medicament records. Each respective insulin medicament record 214 in the first plurality of insulin medicament records comprises: (i) a respective insulin medicament injection event 216 including an amount of insulin medicament injected 218 into the subject using a respective insulin pen 104 of one or more insulin pens used by the subject, (ii) a corresponding insulin medicament injection event timestamp 220 for the respective insulin medicament injection event, and (iii) a respective type of insulin medicament 222 injected into the subject from one of (a) a basal insulin medicament and (b) a bolus insulin medicament.

In some embodiments, the basal insulin medicament specified by one or more insulin medicament records 214 in the second dataset 212 consists of a single insulin medicament having a duration of action that is between 12 and 24 hours or a mixture of insulin medicaments that collectively have a duration of action that is between 12 and 24 hours. Examples of such basal insulin medicaments include, but are not limited to, Insulin DEGLUDEC (developed by NOVO NORDISK under the brand name Tresiba), NPH (Schmid, 2007, "New options in insulin therapy," J Pediatria (Rio J). 83(Suppl 5): S146-S155), GLARGINE (LANTUS, Mar. 2, 2007), Insulin GLARGINE [rDNA origin] injection (Dunn et al. 2003, "An Updated Review of its Use in the Management of Diabetes Mellitus" Drugs 63: p. 1743), and Determir (Plank et al., 2005, "A double-blind, randomized, dose-response study investigating the pharmacodynamic and pharmacokinetic properties of the long-acting insulin analog detemir," Diabetes Care 28:1107-1112).

In some embodiments, the bolus insulin medicament optionally specified by one or more insulin medicament records 214 in the second dataset 212 comprises a single insulin medicament having a duration of action that is between three to eight hours or a mixture of insulin medicaments that collectively have a duration of action that is between three to eight hours. Examples of such basal insulin medicaments include, but are not limited, to LISPRO (HU-MALOG, May 18, 2001, insulin LISPRO [rDNA origin] injection, Indianapolis, Ind.: Eli Lilly and Company), ASPART (NOVOLOG, July 2011), insulin ASPART [rDNA origin] injection, Princeton, N.J., NOVO NORDISK Inc., July, 2011), and GLULISINE (Helms Kelley, 2009, "Insulin glulisine: an evaluation of its pharmacodynamic properties and clinical application," Ann Pharmacother 43:658-668), and Regular (Gerich, 2002, "Novel insulins: expanding options in diabetes management," Am J Med. 113:308-316).

Blocks 412-420. The present disclosure contemplates a number of user scenarios in which the systems and methods of the present disclosure can be applied.

In one such user scenario, for subjects desiring improved titration and having poor blood glucose, a health care practitioner prescribes a subject an insulin medicament (e.g., a basal insulin medicament and/or a combination of a basal and a bolus insulin medicament) for the first time course, and in addition prescribes a "Connect and Control Pack" which is a form of a basal adjustment module 204 for downloading onto a smart phone. This Connect and Control Pack is used to teach patient how to titrate the insulin medicament. In some embodiments, the Connect and Control Pack, in the form of the basal adjustment module 204, is downloaded at the clinic or at home as an application onto the subject's smart phone, which serves as a basal titration adjustment device 250. At home, after picking up the insulin medicament prescription, the subject pairs sensors 102 to the smartphone via the basal adjustment module 204 and registers via a barcode. The basal adjustment module 204 gives patients instructions for the titration process and instructions for syncing data periodically. On a recurring basis, (e.g., every 3 days), the subject receives message from the basal titration adjustment device 250 to scan the continuous glucose measurements from the device 102 and adjust the insulin medicament dose based on data. Insulin medicament dose adjustment is done automatically in the basal adjustment module 204. In some embodiments, the health care practitioner can see the patient's data (e.g., the glucose measurements and the new calculated insulin medicament dosage) via the Internet, as this data is automatically uploaded to a server.

In another user scenario, for subjects desiring having poorly controlled blood glucose values, the health care practitioner sees a subject and prescribes the "Connect and Control Pack," which is one form of the basal adjustment module 204 to troubleshoot and get blood glucose values under control. A demonstration version of the module is used to teach the subject how to use the application, and a full version of the basal adjustment module 204 is downloaded onto the subject's smartphone at the clinic (or at the subject's home). In such scenarios, the smart phone serves as the basal titration adjustment device 250. At home, after picking up the insulin medicament prescription, the subject pairs one or more glucose sensors 102 to the smartphone via app and registers via a barcode. The basal adjustment module 204 gives the subject instructions for syncing data periodically and sending this data to the health care practitioner. The subject wears a continuous glucose monitor for a period of time (e.g., 1 week) and injects the insulin medicament as usual. After this period of time, the doctor looks at data and makes recommendations on the insulin medicament dosage. The subject adjusts treatment in accordance with these recommendations and the health care practitioner follows progress until the blood glucose is under control. The subject then stops wearing the continuous glucose monitor and removes the pen add-on device when the blood glucose is under control.

Figure 7:
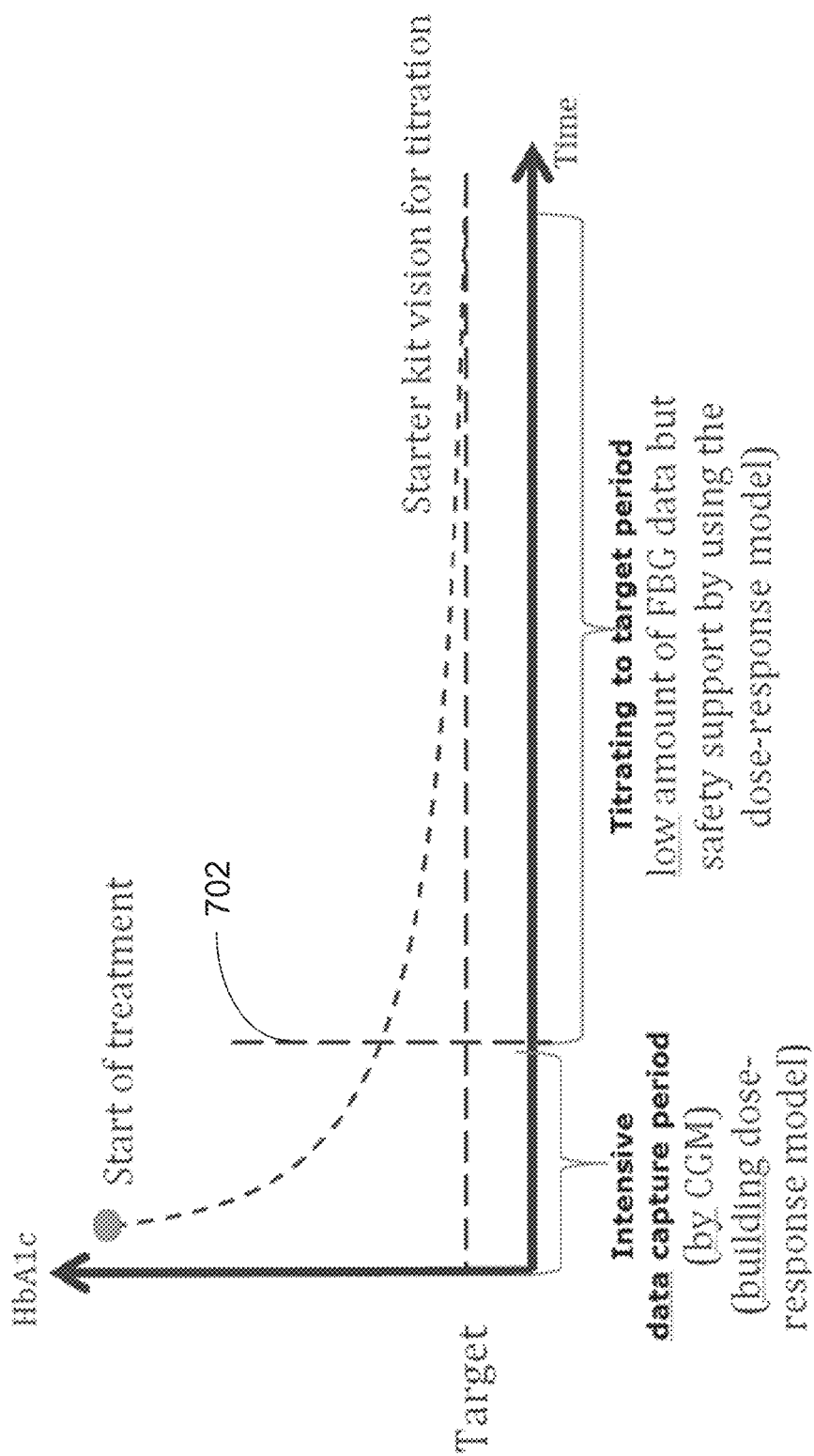
FIG. 7 illustrates a titration curve for a subject that brings the subject to a target HbA1c value using insulin medicaments over time, in which there is an intensive data capture period followed by a period in which less intensive measurement is made in accordance with an embodiment of the present disclosure.

Advantageously, the present disclosure provides a new element to the above user scenarios. The new element is to divide the data capture into two parts, an intensive data capture period followed by a less intensive period. Blocks 402 through 410 describe the intensive data capture period during a first time course, which is referred to in FIG. 7 as an intensive data capture period and occupies the region of the titration curve to the left of line 702. Referring to block 412 of FIG. 4B, in the method, the first dataset 206 and the second dataset 212 are used to calculate a first glycaemic risk measure 234 and an insulin sensitivity factor 236 of the subject during the first time course in order to transition to the second time course of FIG. 7, on the right side of line 702.

Figure 9:
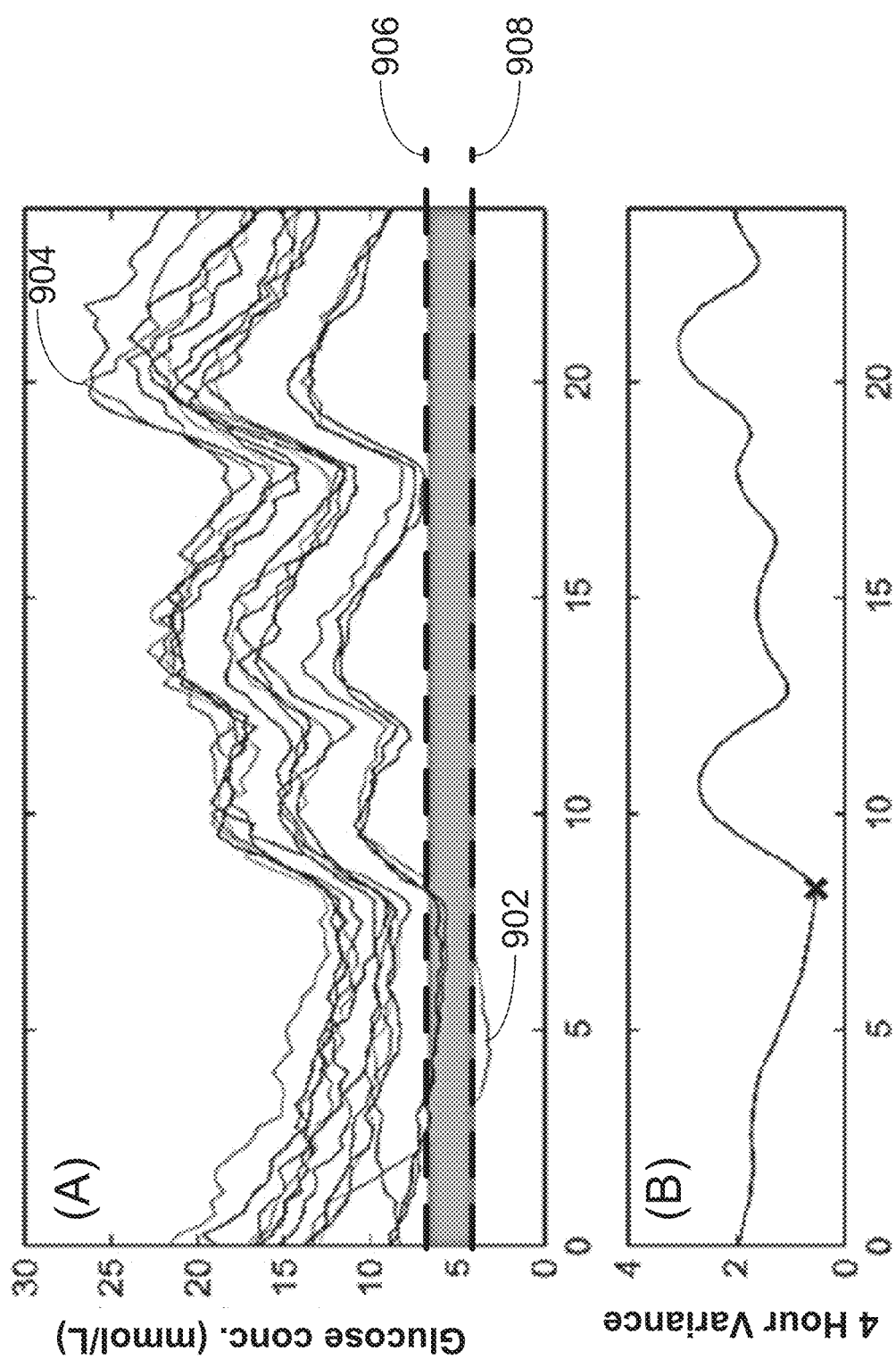
FIG. 9 illustrates exemplary data that is collected in a first time course in accordance with an embodiment of the present disclosure. Each line in panel A represents glucose levels of a subject during a corresponding 24 hour period during the first time course. Panel B illustrates the average running 4 hour variance of the glucose data of panel A.

The first time course, as summarized above in blocks 402 through 410, constitutes a starter period where the data capturing of blood glucose and insulin data is intensive. In one embodiment, a continuous glucose monitor is used 14 days with readings every 5 minutes to produce the first dataset 206. The outcome of this dataset is large enough to robustly enable a system identification of the user's dose-response and a profile of the blood glucose profile and daily variance. FIG. 9 illustrates. Panel A of FIG. 9 shows glucose concentration over the 14 day period, where the autonomous glucose measurements from each day are plotted on top of each other over the course of a recurring 24 hour period. Panel B of FIG. 9 shows the average running 4 hour variance, and an identified time of minimum variance. Then, a secondary period, the second time course where the profile from the starter period (the first time course) is used to guide the subject in titrating to the target glucose levels. This less data-intensive titration period (to the right of line 702 in FIG. 7) allows for data capture to be reduced to a much lower level, simplifying the treatment and reducing the burden of compliance.

Figure 12:
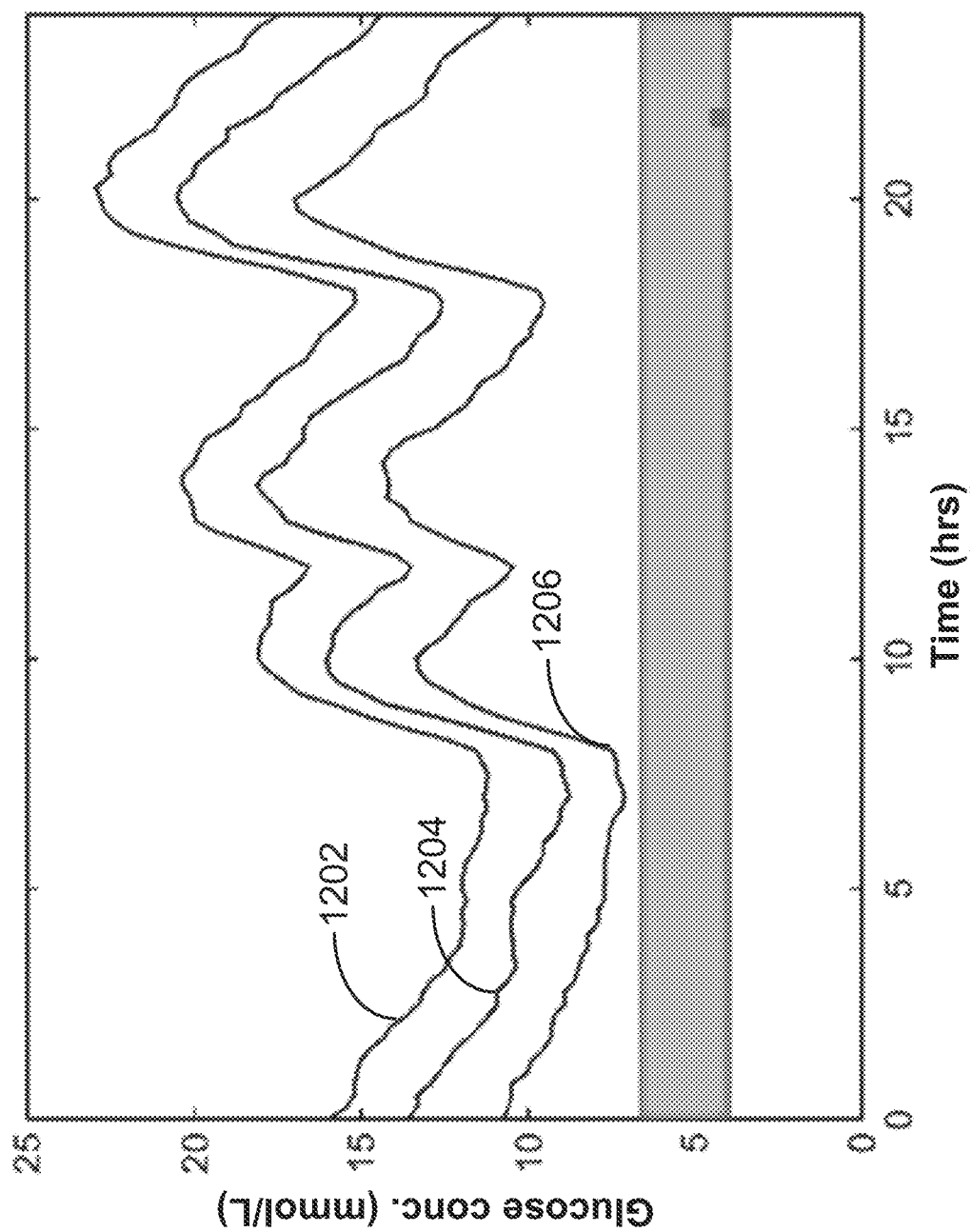
FIG. 12 illustrates how three different insulin medicament dose sizes are given to the subject during the first time course, where the average glucose values during each period are used to estimate the insulin sensitivity and predict change in glucose concentration during does change in accordance with an embodiment of the present disclosure.

Referring to block 414 and FIG. 9, in some embodiments, the first dataset 206 and the second dataset 212 is used to calculate the first glycaemic risk measure of the subject during the first time course by determining: (i) a total glucose level variability observed across the plurality of autonomous glucose measurements, (ii) a plurality of fasting glucose levels calculated from the plurality of autonomous glucose measurements, (iii) a minimum glucose measurement 902 observed in the plurality of autonomous glucose measurements, (iv) a maximum glucose measurement 904 observed in the plurality of autonomous glucose measurements, (v) a rate of change in the insulin sensitivity factor calculated using the plurality of autonomous glucose measurements and the second dataset 212, (vi) a basal adherence score over the first time course that is computed by dividing (a) a number of insulin medicament injection events 216 that were taken by the subject when dictated by the standing insulin regimen 224 by (b) a total number of basal insulin medicament injection events 216 dictated by the standing insulin regimen 224 in the first time course, (vii) a percentage of the time glucose levels of the subject are above a first target range 906-908 (e.g., referring to FIG. 9, the target range being glucose concentrations that are between line 906 and 908) across the plurality of autonomous glucose measurements, (viii) a percentage of the time glucose level of the subject are below the first target range 906-908 across the plurality of autonomous glucose measurements, (ix) a percentage of the time the glucose level of the subject is outside (above or below) the first target range 906-908 across the plurality of autonomous glucose measurements, (x) a measure of spread of the plurality of autonomous glucose measurements (e.g., delta between the highest glucose measurement and lowest glucose measurement in the first time course), or (xi) a mean profile and standard deviation of the glucose measurements in the first time course. FIG. 12 illustrate a mean profile and standard deviation of the glucose measurements in the first time course.

In some embodiments, the first glycaemic risk measure is based upon autonomous glucose measurements in the first dataset that occur during periods of fasting. There are many ways to ascertain such a fasting period. In some embodiments, the identifying of the fasting period comprises receiving a fifth dataset 322 from a wearable device (e.g., from wearable physiological measurement devices, from measurement devices within the data collection device 200 such as a magnetometer or a thermostat, etc.), and the fifth dataset indicates an auxiliary metric of the user during the first time course that is indicative of a fasting period. In some embodiments, the auxiliary data 324 is body temperature of the subject. In some embodiments, the auxiliary data 324 is a measurement of activity of the subject. In some embodiments, the optional accelerometer 317, optional GPS 319, and/or magnetometer (not shown) of the basal titration adjustment device 250 or such components optionally within the one or more glucose monitors 102 and/or the one or more insulin pens 104 is used to acquire such auxiliary data 324. In some embodiments, both an autonomous fast detection algorithm, such as one disclosed in block 416 below, and the auxiliary data measurements are used for detecting the fasting period. For instance, in some embodiments, a fasting period is autonomously detected (e.g., by way of block 416) and verified using the auxiliary data 324. To illustrate, when a period of fasting is autonomously detected using an algorithm such as one disclosed in block 416, it is matched in time (temporally matched) to the auxiliary data 324 which further indicate that the subject is fasting. When this match is successful, the period of fasting is deemed verified and used in further steps of the present disclosure.

Figure 4B:
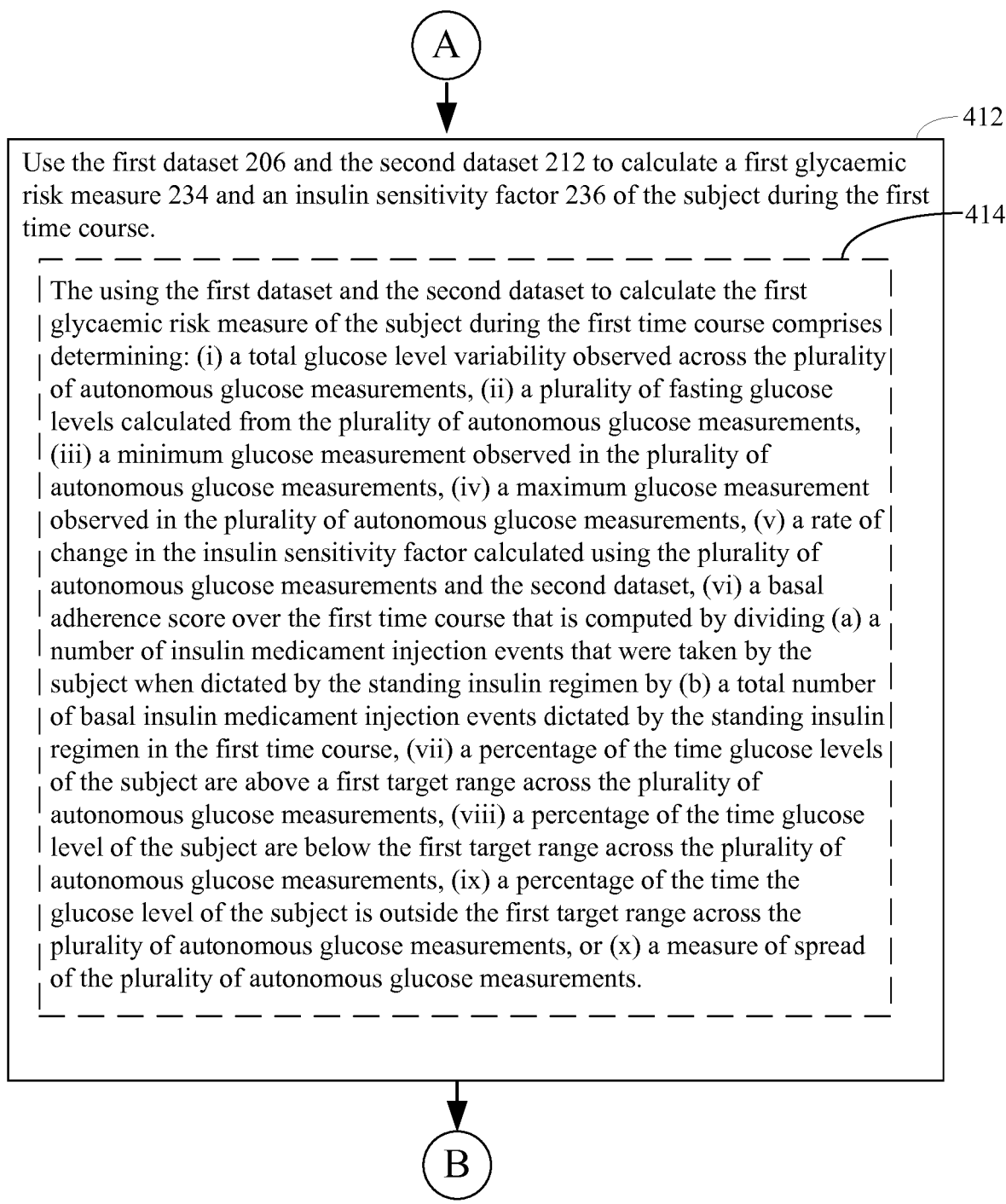
Figure 4C:
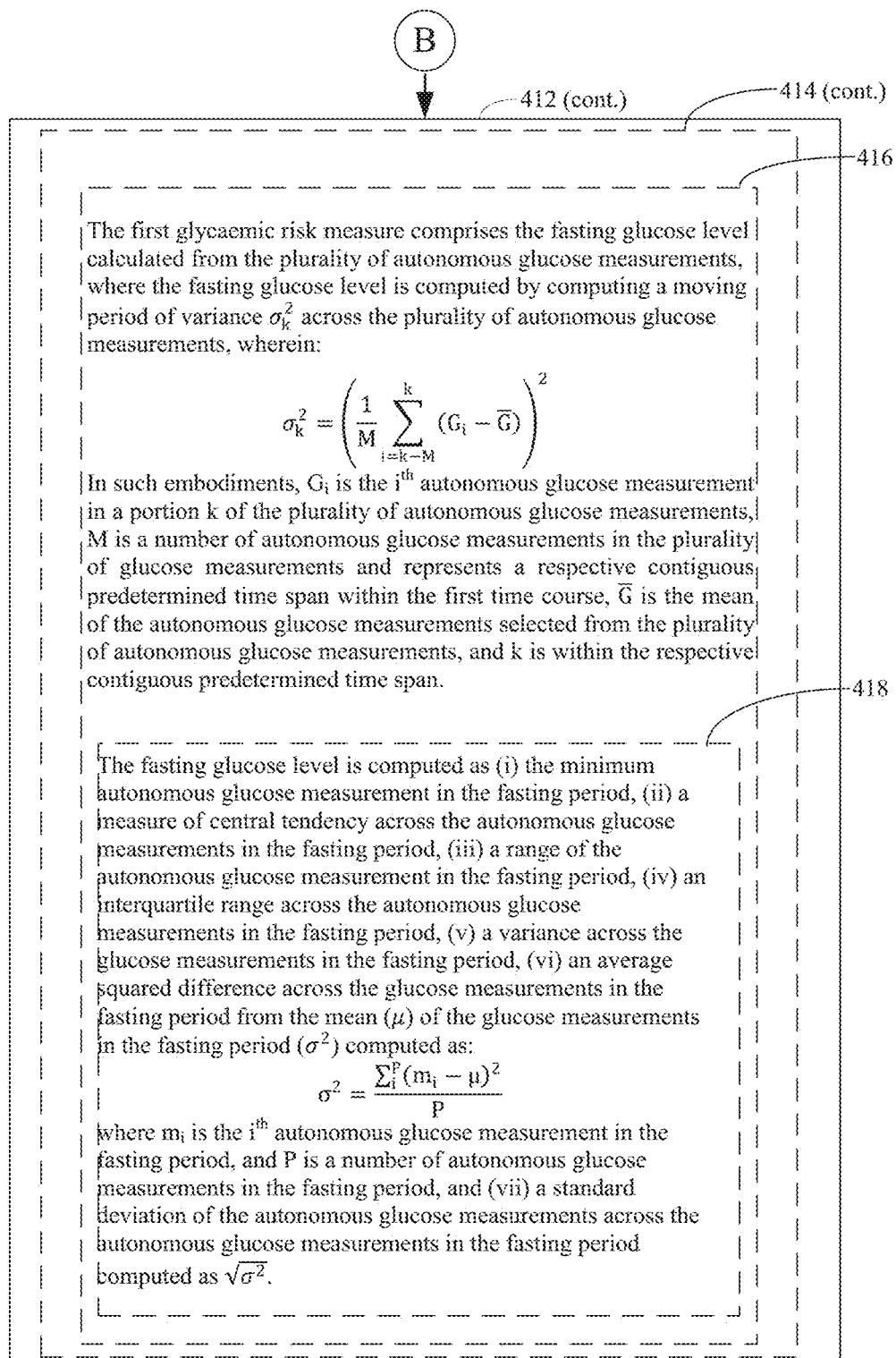
Figure 4F:
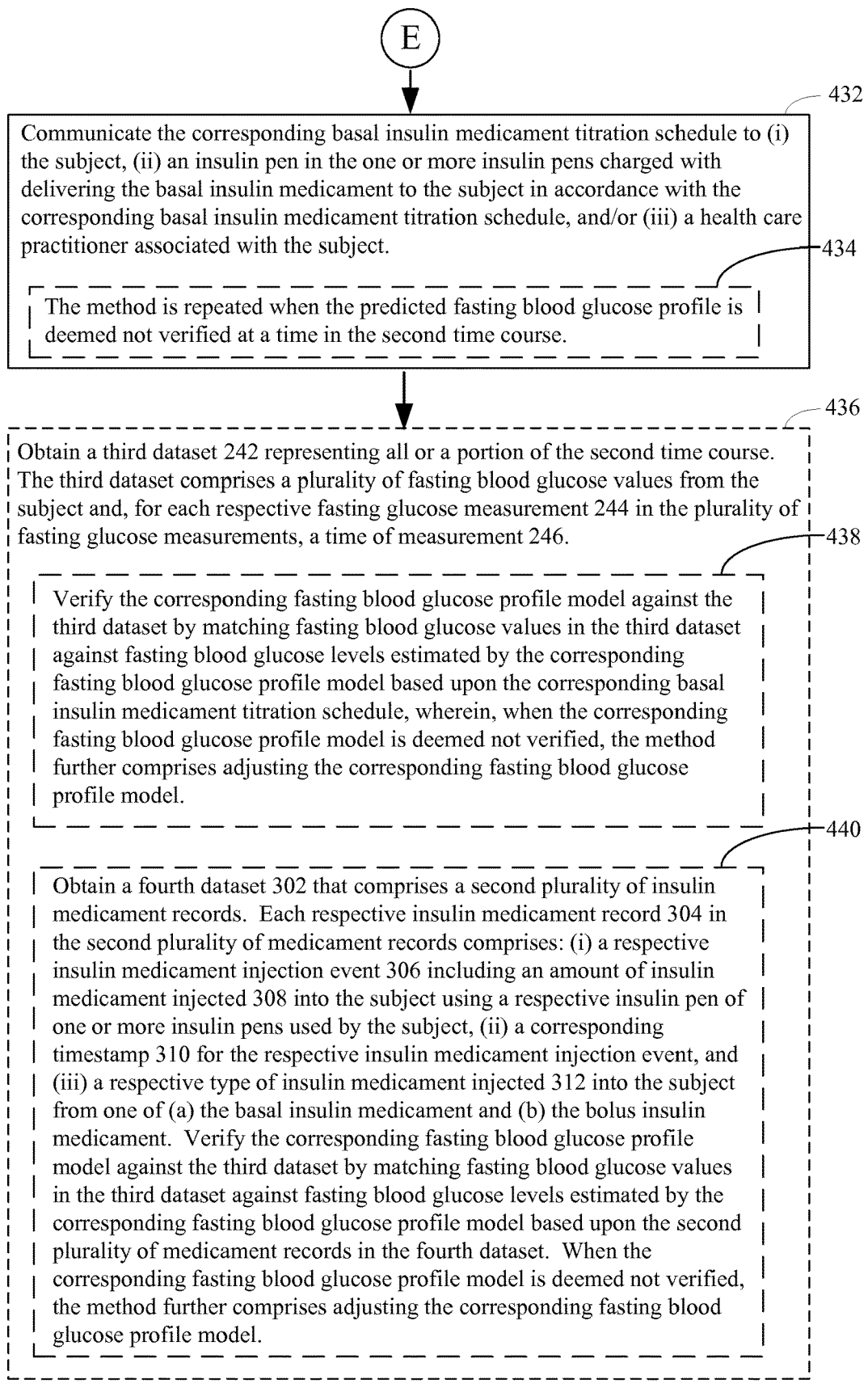

Referring to block 416 of FIG. 4C, in some embodiments, the first glycaemic risk measure comprises a fasting glucose level calculated from the plurality of autonomous glucose measurements. Thus, in some embodiments the plurality of autonomous glucose measurements is evaluated to identify a fasting period, and the autonomous glucose measurements in this fasting period are then used to determine the fasting glucose level.

For instance, consider the case of the plurality of fasting glucose measurements plotted in FIG. 9. To detect the fasting glucose level, the period of lowest variance in the autonomous glucose measurements and the mean value lower than the mean glucose measurement of the same day is found. Panel B of FIG. 9 shows a running four hour variance in autonomous glucose measurement over the 14 days plotted in panel A of FIG. 9 (an example for the first time course), defined by $$\sigma_k^2 = \frac{1}{M} \sum_{i=k-M+1}^{k} (G_i - \overline{G})^2$$

Figure 10:
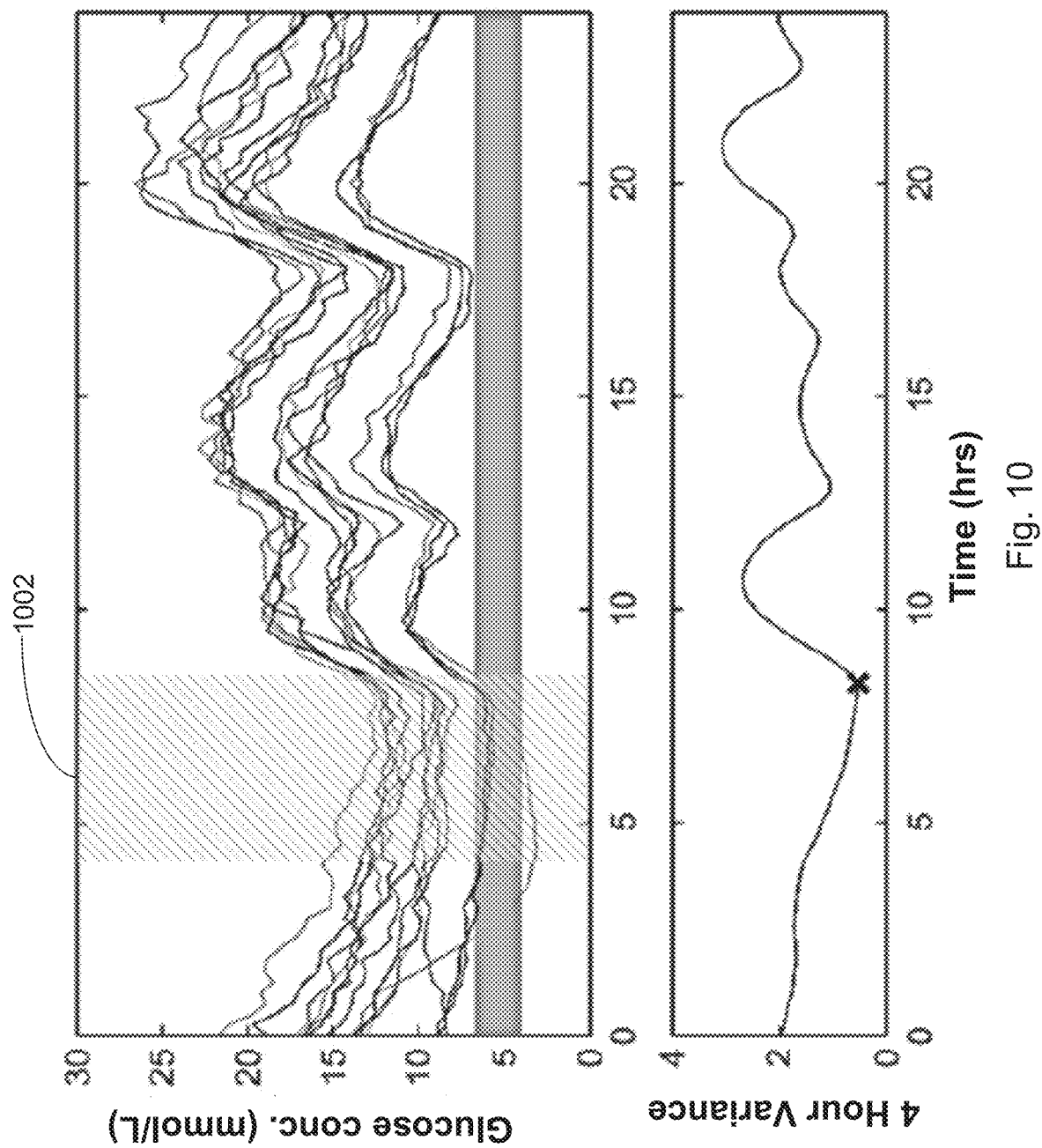
FIG. 10 illustrates how the four hours prior to the identified minimum running variance of Panel B of FIG. 9 is used as the source of fasting glucose values in accordance with an embodiment of the present disclosure. This period is used to estimate hypoglycaemic risk. In this case, a hypoglycaemic event occurred once during the first time course.
Figure 11:
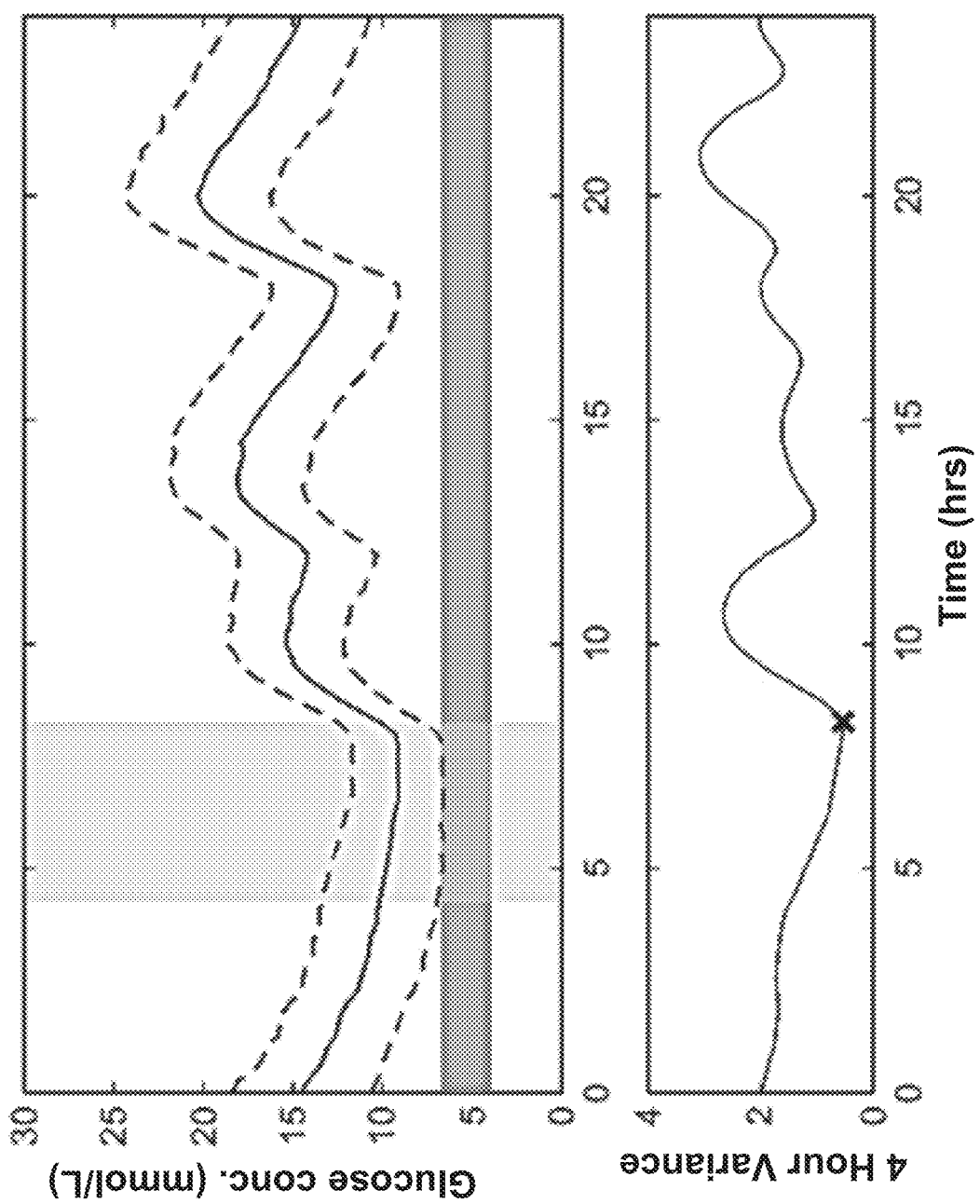
FIG. 11 illustrates how the mean profile and standard deviation of the glucose measurements made during the first time course are used to determine glycaemic risk of the subject during the first time course in accordance with an embodiment of the present disclosure.
Figure 13:
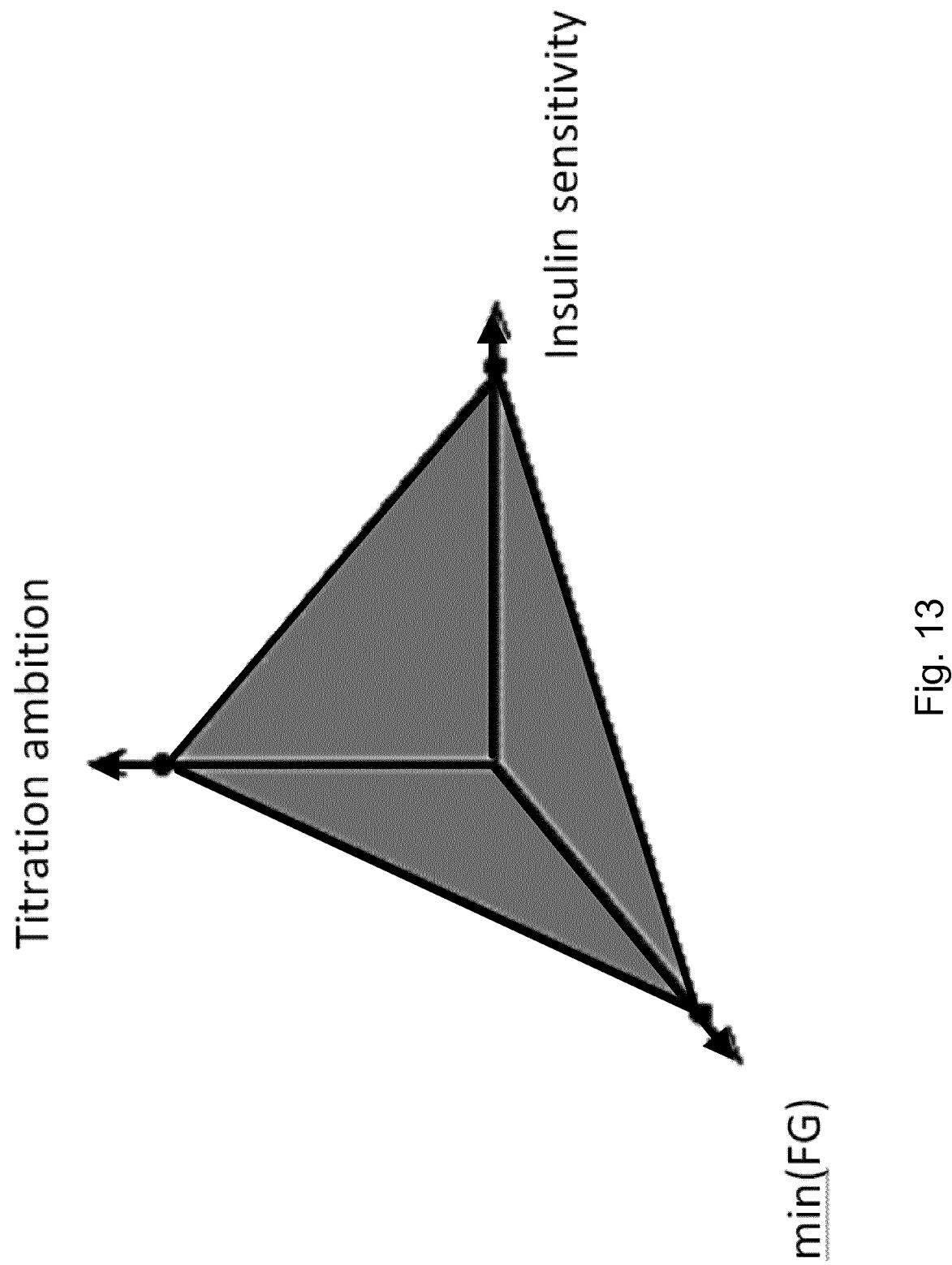
FIG. 13 illustrates how the titration ambition level of a basal insulin medicament titration schedule is a function of insulin sensitivity and minimum fasting glucose in accordance with some embodiments of the present disclosure.

As such, a fasting glucose level during the first time course is computed by computing a moving period of variance $\sigma_k^2$ across the plurality of autonomous glucose measurements of the first time course, where $G_i$ is the $i^{th}$ autonomous glucose measurement in a portion k of the plurality of autonomous glucose measurements, M is a number of autonomous glucose measurements in a given time span (e.g. a running four hour window across the 24 hour period plotted in FIG. 9) and represents a respective contiguous predetermined time span in the 24 hour time period, $\overline{G}$ is the mean of the autonomous glucose measurements selected from the plurality of autonomous glucose measurements, and k is within the respective contiguous predetermined time span. A fasting period in the first time course is associated with a period of minimum variance $$\min_{k} \sigma_k^2$$

within the first time course. The fasting glucose level is computed using the glucose measurements in the plurality of autonomous glucose measurements in the fasting period. In the example of FIG. 9, the four hours prior to 8 AM have the lowest variance and a mean value less than the mean glucose concentration of the 24 hours and thus is considered the fasting period 1002, as illustrated in FIG. 10. The autonomous glucose measurements in period 1002 are therefore used to determine a fasting glucose level that represents the fasting period in the first time course. This fasting glucose level, in turn, is used to determine how ambitious the basal insulin medicament titration schedule should be, as illustrated in FIG. 13 and discussed in greater detail below, in the case where the fasting glucose level is computed as the minimum autonomous glucose measurement in the fasting period (min(FG)). This fasting glucose level is further used to determine how often blood glucose levels should be measured during the second time course, based on the minimum value of the blood glucose measurement within the fasting period (e.g. whether hypos occurred) and variance of the blood glucose measurements in the fasting period.

Referring to block 418 of FIG. 4C, in some embodiments, the fasting glucose level comprises (i) the minimum glucose level from the autonomous glucose measurements in the fasting period, (ii) a measure of central tendency across the autonomous glucose measurements in the fasting period (e.g., an arithmetic mean, weighted mean, midrange, midhinge, trimean, Winsorized mean, median, or mode of the autonomous glucose measurements in the fasting period), (iii) a range of the autonomous glucose measurements in the fasting period (e.g., delta between the highest glucose measurement and lowest glucose measurement in the fasting period), (iv) an interquartile range across the autonomous glucose measurements in the fasting period, (v) a variance of the autonomous glucose measurements in the fasting period, (vi) an average squared difference across the autonomous glucose measurements in the fasting period from the mean (μ) of the autonomous glucose measurements in the fasting period ($\sigma^2$) computed as:

$$\sigma^2 = \frac{\sum_{i}^{P}(m_i - \mu)^2}{P}$$

where $m_i$ is the $i^{th}$ autonomous glucose measurement in the fasting period, and P is a number of autonomous glucose measurements in the fasting period, and (vii) a standard deviation across the autonomous glucose measurements in the fasting period computed as $\sqrt{\sigma^2}$.

As discussed above, the first dataset 206 and the second dataset 212 are used to calculate a first glycaemic risk measure 234 and an insulin sensitivity factor 236 of the subject during the first time course. Blocks 414 through 418 disclose ways in which the first glycaemic risk measure 234 is computed in some embodiments. In some embodiments, insulin sensitivity is determined based on the fasting glucose values and the corresponding insulin doses:

$$ISF = \frac{\Delta FG}{\Delta U}$$

where ISF is the insulin sensitivity FG is fasting glucose and U is insulin medicament dose size. Thus, to compute ISF, varying doses of insulin medicament need to be administered during the first time course. FIG. 12 illustrates an embodiment in which the first time period is broken up into three periods (dosing period 1202, dosing period 1204, and dosing period 1206), and a different insulin dosage size is prescribed in each dosing period. In FIG. 12, the autonomous glucose measurements over a 24 hour period are plotted for each dosing period. The average glucose values during the fasting period in each dosing period, combined with the insulin medicament dose sizes for each dosing period are used to compute the insulin sensitivity.

Referring to block 420, in some embodiments the standing insulin regimen 224 for the subject over the first time course specifies a plurality of epochs (n) (e.g., dosing periods) within the first time course, and a different daily (or other recurring period such as 12 hour, 48 hour, weekly) total basal insulin medicament dosage for each respective epoch in the plurality of epochs. In such embodiments, the insulin sensitivity factor (ISF) is calculated by:

$$ISF = \left(\frac{1}{\left(\frac{n!}{(n-2)!}\right)}\right) \sum_{n, i \neq j}^{\frac{n!}{(n-2)!}} \frac{\Delta FG_{i,j}}{\Delta U_{i,j}}$$

where i is a first index into the plurality of epochs, j is a second index into the plurality of epochs, $\Delta FG_{i,j}$ is the difference in average fasting glucose level of the subject between epoch i and epoch j, and $\Delta U_{i,j}$ is the difference in daily (or other recurring period such as 12 hour, 24 hour, weekly) insulin dose size of the subject between epoch i and epoch j as determined by the standing insulin regimen or the second dataset. For instance, if the standing insulin regimen is used to compute $\Delta U_{i,j}$, adherence to the standing insulin regimen by the subject is assumed. On the other hand, if the second dataset is used to determine or confirm $\Delta U_{i,j}$, then adherence by the subject to the standing insulin regimen does not have to be assumed. Rather, the insulin dose size of the subject may be directly computed from the second dataset. For instance, the insulin medicament records 214 having timestamps 220 in each of the epochs may be used to compute the insulin dose size for each epoch.

Blocks 422-430. Referring to block 422 of FIG. 4D, the method continues by using at least the first glycaemic risk measure 234 and the insulin sensitivity factor 236 of the subject to obtain (i) a corresponding basal insulin medicament titration schedule 238 for a second time course for the subject, where the second time course occurs subsequent to the first time course, and (ii) a corresponding fasting blood glucose profile model 240 over the second time course for the subject based on the corresponding basal insulin medicament titration schedule. The corresponding fasting blood glucose profile model 240 predicts the fasting blood glucose level of the subject based upon an amount of basal insulin medicament injected into the subject.

In some embodiments, the basal insulin medicament titration schedule 238 for a second time course for the subject is identified using the first glycaemic risk measure 234 and the insulin sensitivity factor 236 of the subject. The basal insulin medicament titration schedule 238 is customized as a function of titration ambition or titration ambition level defined in different ways:

Titration ambition=f(x), where,

Titration ambition=[Dose change frequency,Dose change step sizes,FG measurement frequency]

based upon f(x) which is a function of the first glycaemic risk measure 234 and the insulin sensitivity factor 236 (x=[first glycaemic risk measure, ISF, . . . ]). The basal insulin medicament titration schedule 238 can be specified as dose change frequency and dose change step sizes, as indicated above, or as a set of corresponding dose times and dose sizes. In some embodiments, additional variables are used for x. For instance, in some embodiments x=[min(BG),var(BG),Glycaemic risk, . . . ], and where BG alternatively stands for the plurality of autonomous glucose measurements in the first dataset 206 or the autonomous glucose measurements in the fasting period and where the different factors of titration ambition are restricted to be within a predefined range. Here Glycaemic risk denotes additional risk measures. FIG. 13 illustrates an example of how titration ambition can be a function of insulin sensitivity and minimum fasting glucose (min(FG))).

Figure 14:
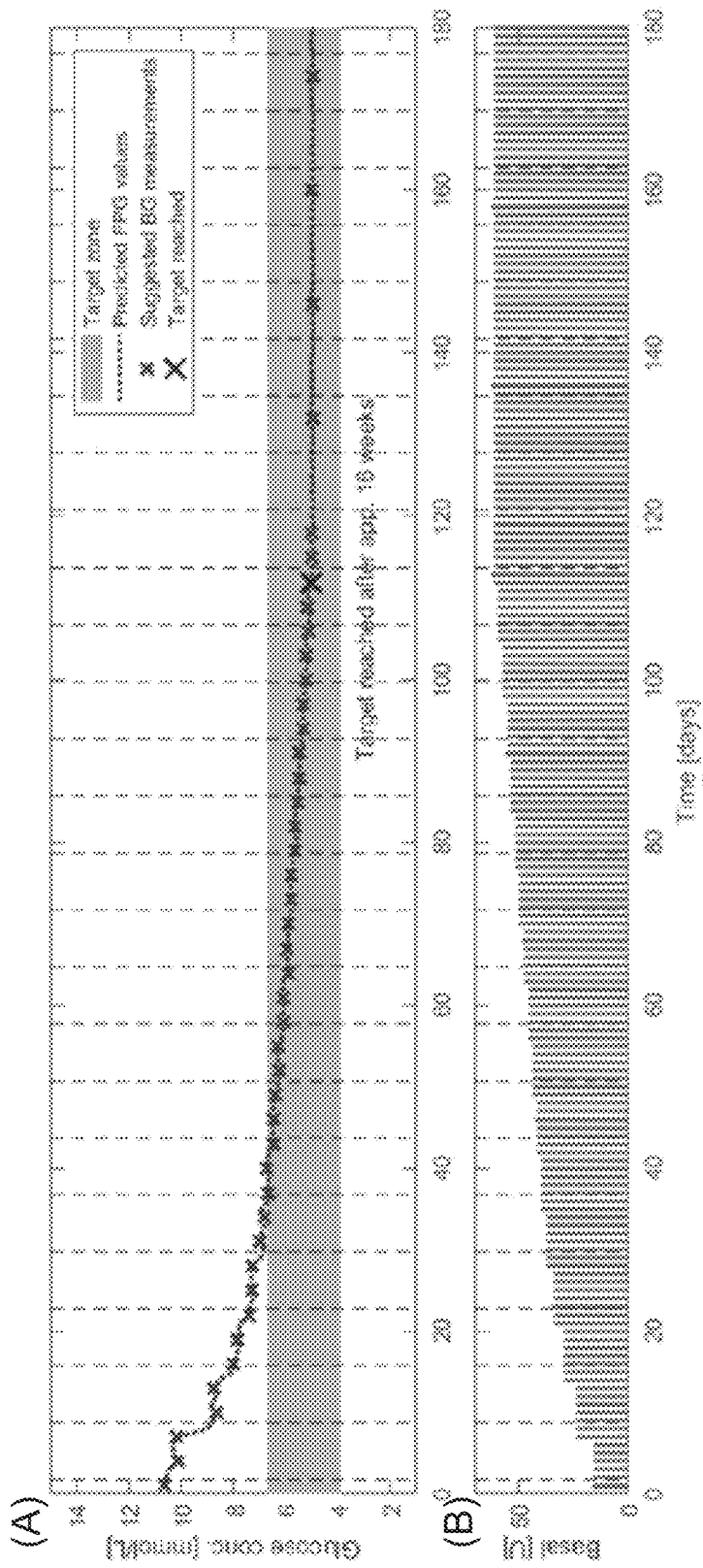
FIG. 14 shows a fasting blood glucose profile model (Panel A) that predicts the fasting glucose concentration of one subject as a function of the units of basal insulin medicament in a corresponding basal insulin medicament titration schedule (Panel B) for one subject in accordance with an embodiment of the present disclosure.
Figure 15:
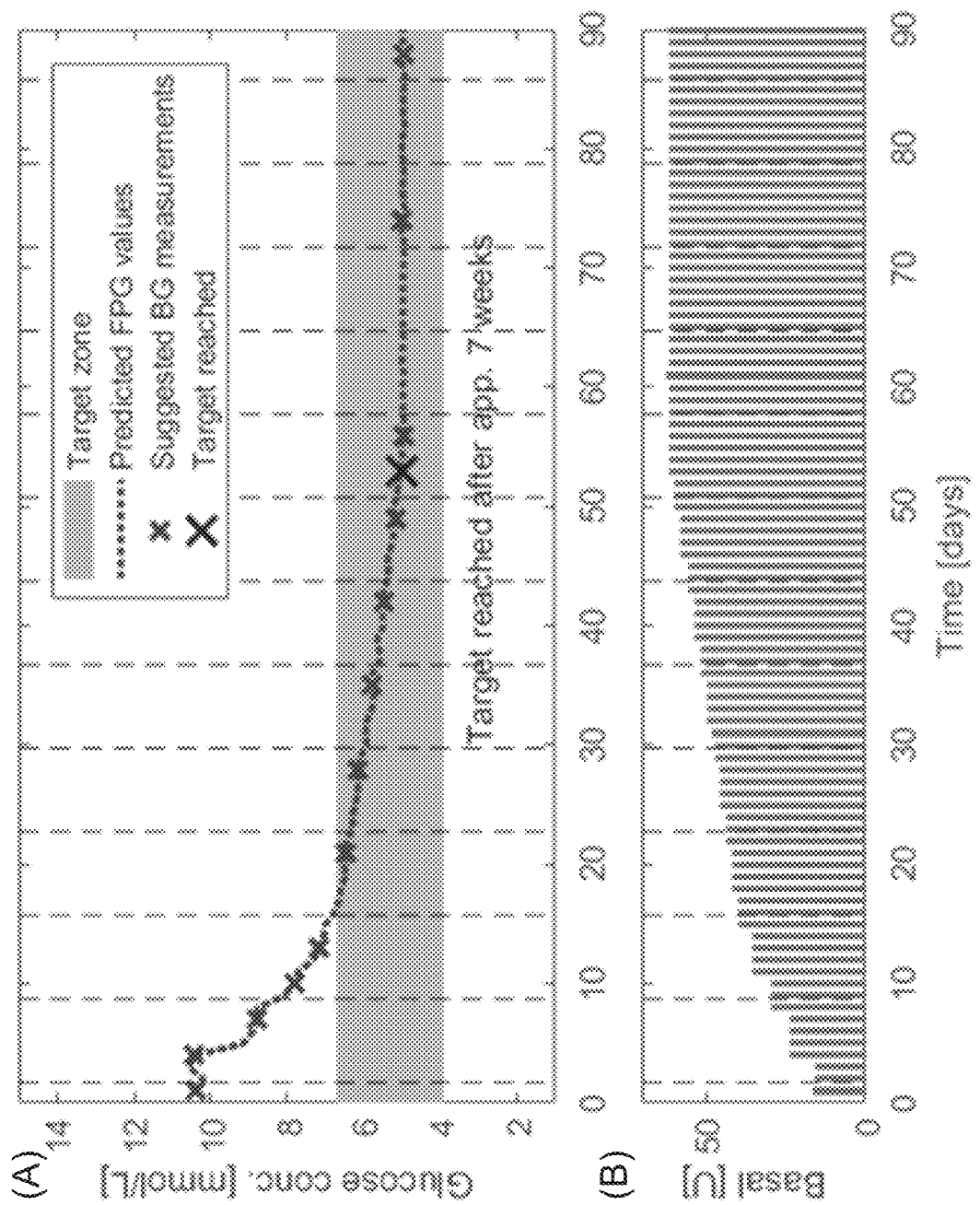
FIG. 15 shows a fasting blood glucose profile model (Panel A) that predicts the fasting glucose concentration of another subject as a function of the units of basal insulin medicament in a corresponding basal insulin medicament titration schedule (Panel B) for one subject in accordance with an embodiment of the present disclosure.

The basal insulin medicament titration schedule 238 can be evaluated using the result of the calculated titration ambition, where the time of dose can be a function of a predefined initial daily dose time and the dose change frequency, e.g., take a daily basal dose in the morning and increase the dose every third day, and the dose can be a function of a predefined initial dose and the dose change step size, e.g., increase the dose by 2 units for each instance of dose change, i.e, every third day. Alternatively the basal insulin medicament titration schedule 238 could specify the illustrated titration schedule of FIGS. 14 and 15, illustrating a dose size as a function of time. As discussed above in relation to blocks 402 through 410, in some embodiments, the input of data in the intensive data capture (first time course) period is insulin data captured through connected pen or manual input (e.g., the second dataset 212), glucose measurement (fasting glucose measurement, continuous glucose measurement) (e.g., the first dataset 206), and possibly others, such as wearable sensors to measure (energy measure), weight, age, meal data, habits (activity), and/or advanced blood analysis. For example, referring to block 424, in some embodiments, a fifth dataset 322 is obtained. The fifth dataset comprises auxiliary data 324 associated with the subject in the first time course. The auxiliary data comprises one or more of energy exerted by the subject, subject weight, subject age, and subject meal activity during the first time course. In some embodiments, the fifth dataset is used in conjunction with the first glycaemic risk measure and the insulin sensitivity factor of the subject to obtain the corresponding basal insulin medicament titration schedule 238 and the corresponding fasting blood glucose profile model 240 over the second time course. For instance, in some embodiments, this auxiliary data is used in the vector x to ascertain titration ambition for the basal insulin medicament titration schedule.

FIG. 14 and FIG. 15 respectively correspond to two different subjects having different values for the first glycaemic risk measure 234 and therefore different basal insulin medicament titration schedules 238. The different basal insulin medicament titration schedules 238 have different titration ambition levels.

Panel B of FIG. 14 shows a slow and careful basal insulin medicament titration schedule 238 over the second time course for a subject with high fasting glucose variance and high hypo-risk. Panel A of FIG. 14 shows the corresponding fasting blood glucose profile model 240 that predicts the fasting glucose concentration of the subject as a function of the units of basal insulin medicament in the basal insulin medicament titration schedule 238. To validate this basal insulin medicament titration schedule 238 during the second time course, the subject is instructed to measure fasting glucose every three days throughout the first 16 weeks (marked by small x's in panel A of FIG. 14), until the target is estimated to be reached. After that, the subject fasting glucose may be measured every two weeks.

Panel B of FIG. 15 shows an ambitious basal insulin medicament titration schedule 238 over the second time course for a subject with low fasting glucose variance, low insulin sensitivity and low hypo-risk. Panel A of FIG. 15 shows the corresponding fasting blood glucose profile model 240 that predicts the fasting glucose concentration of the subject as a function of the units of basal insulin medicament in the basal insulin medicament titration schedule 238. The target glucose value is assumed to be reached in the seventh week, and, to validate this basal insulin medicament titration schedule 238 during the second time course, the subject is instructed to measure the fasting glucose every three days for the first two weeks of the second time course, then every week for the next five weeks, and once every two weeks after reaching target glucose levels until the titration period is stopped by, for example, the health care practitioner.

When the titration period has been initiated and the patient measures the fasting glucose, these measurements are used to monitor the titration during the second time course. If the measurements fall within a predicted fasting glucose range, the titration proceeds as planned. If the measurements are not as expected, the titrator could e.g. decrease the ambition plan and adjust the titration according to that. In some embodiments, if the measurements are not as expected, the subject is requested to reengage in the intensive measurement period of the first time course, that is blocks 404 through 430 are repeated.

Figure 3B:
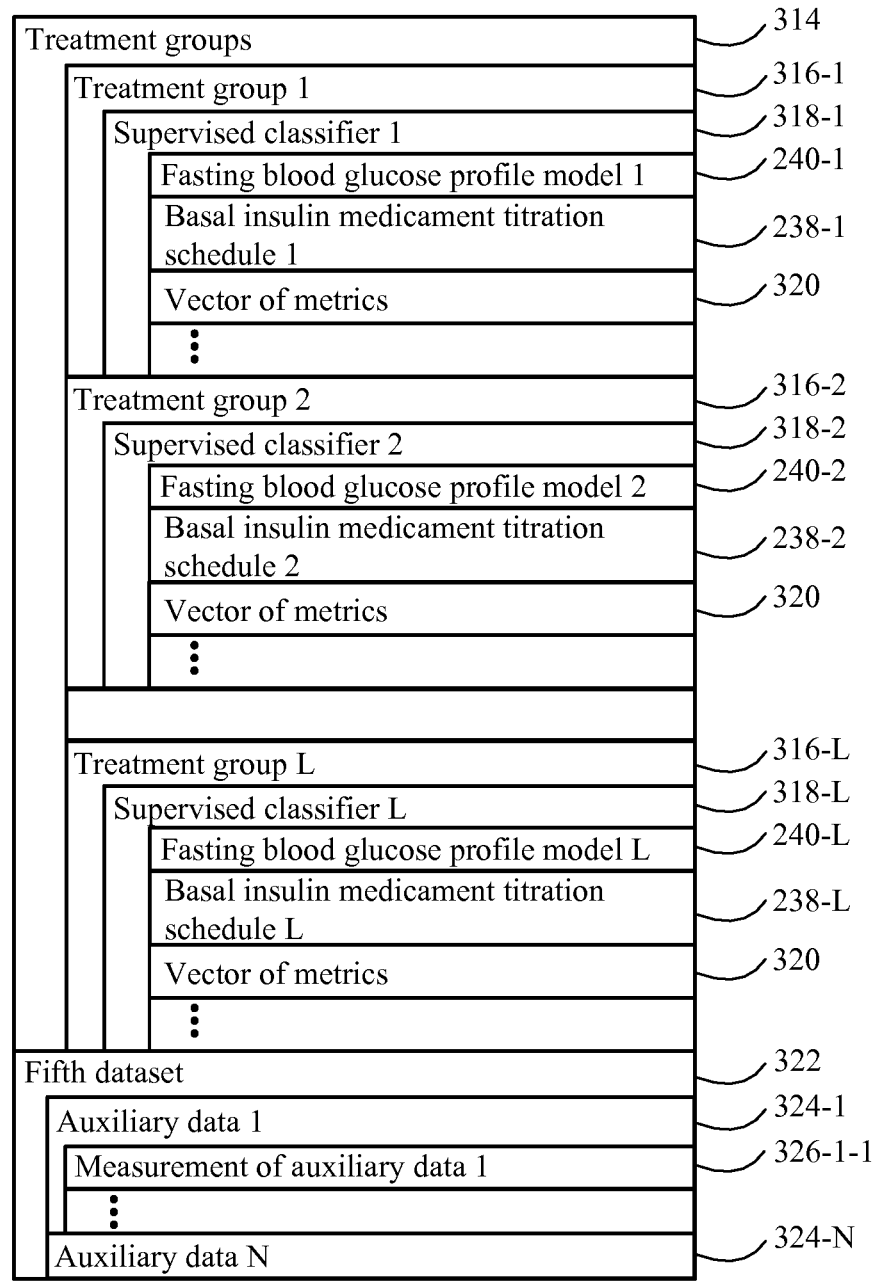

Referring to block 426 of FIG. 4E, in some embodiments, the using at least the first glycaemic risk measure and the insulin sensitivity factor of the subject comprises identifying a first treatment group 316 in a plurality of treatment groups. As illustrated in FIG. 3B, each respective treatment group in the plurality of treatment groups is independently associated with a corresponding supervised classifier 318 in a plurality of supervised classifiers. The supervised classifier of the first treatment group is used to compute the corresponding fasting blood glucose profile model 240 and the corresponding basal insulin medicament titration schedule 238 for the second time course for the subject, thereby obtaining the corresponding basal insulin medicament titration schedule and the corresponding fasting blood glucose profile model. Referring to block 428, in some embodiments, the identifying the first treatment group in the plurality of treatment groups comprises co-clustering a vector of metrics 320 obtained from at least the first dataset and the second dataset against each treatment group in the plurality of treatment groups thereby obtaining a respective distance score against each treatment group in the plurality of treatment groups. Such treatment groups are themselves determined by clustering the vector of metrics from the intensive data in the first time course (e.g., the first and second datasets) from a population of subjects. In some embodiments, the vector of metrics comprises the first glycaemic risk measure and the insulin sensitivity factor of the subject. Another example of a vector of metrics is x, discussed above and reproduced below:

$$x=[\min(BG), \mathrm{var}(BG), \text{Glycaemic risk}, \ldots].$$

In such embodiments, the first treatment group is identified from among the plurality of treatment groups when the distance score for the first treatment group satisfies a confidence threshold.

Clustering is described on pages 211-256 of Duda and Hart, *Pattern Classification and Scene Analysis*, 1973, John Wiley & Sons, Inc., New York, (hereinafter "Duda 1973") which is hereby incorporated by reference in its entirety. As described in Section 6.7 of Duda 1973, the clustering problem is described as one of finding natural groupings in a dataset. To identify natural groupings, two issues are addressed. First, a way to measure similarity (or dissimilarity) between two samples (vector of metrics) is determined. This metric (similarity measure) is used to ensure that the samples (e.g., vectors of metrics from the first time course from a first plurality of subjects) in one cluster are more like one another than they are to samples (vectors of metrics from the first time course from other pluralities of subjects) in other clusters. Second, a mechanism for partitioning the data into clusters using the similarity measure is determined.

Similarity measures are discussed in Section 6.7 of Duda 1973, where it is stated that one way to begin a clustering investigation is to define a distance function and to compute the matrix of distances between all pairs of samples (vectors of metrics from the first time course from subjects) in a dataset. If distance is a good measure of similarity, then the distance between samples in the same cluster will be significantly less than the distance between samples in different clusters. However, as stated on page 215 of Duda 1973, clustering does not require the use of a distance metric. For example, a nonmetric similarity function s(x, x') can be used to compare two vectors x and x'. Conventionally, s(x, x') is a symmetric function whose value is large when x and x' are somehow "similar". An example of a nonmetric similarity function s(x, x') is provided on page 216 of Duda 1973.

Once a method for measuring "similarity" or "dissimilarity" between points in a dataset has been selected, clustering requires a criterion function that measures the clustering quality of any partition of the data. Partitions of the data set that extremize the criterion function are used to cluster the data. See page 217 of Duda 1973. Criterion functions are discussed in Section 6.8 of Duda 1973.

More recently, Duda et al., *Pattern Classification*, $2^{nd}$ edition, John Wiley & Sons, Inc. New York, has been published. Pages 537-563 of the reference describe clustering in detail. More information on clustering techniques can be found in Kaufman and Rousseeuw, 1990, *Finding Groups in Data: An Introduction to Cluster Analysis*, Wiley, New York, N.Y.; Everitt, 1993, *Cluster analysis* (3d ed.), Wiley, New York, N.Y.; and Backer, 1995, *Computer-Assisted Reasoning in Cluster Analysis*, Prentice Hall, Upper Saddle River, N.J. Particular exemplary clustering techniques that can be used in block 428 include, but are not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, Jarvis-Patrick clustering, and steepest-descent clustering.

In some embodiments in block 428, the vector of metrics 320 obtained from at least the first dataset and the second dataset of a subject are clustered against the vector of metrics 320 of each treatment group 316 and the basal insulin medicament titration schedule 238 (and corresponding fasting blood glucose profile model 240) of the treatment group that has best measure of similarity score (e.g., distance metric) to the vector of metrics 320 obtained from at least the first dataset and the second dataset of a subject is selected for the subject.

Referring to block 430 of FIG. 4E, in some embodiments, the basal insulin medicament titration schedule 238 has a fasting blood glucose target (FGL) (239) that is calculated as:

$$\mathrm{FGL}=(w^{*}\mathrm{ISF})+\Sigma_{i}^{N}c_{i}x_{i}$$

where w is a scaling weight, ISF is the insulin sensitivity factor 236 of the subject calculated from the first and second datasets over the first time course, and $c_i$ is an $i^{th}$ weighting constant applied to an $x_i^{th}$ glycaemic risk measure of the subject observed during the first time course, where the $x_i^{th}$ glycaemic risk measure is in a plurality of glycaemic risk measures that includes the first glycaemic risk measure 234, i is an index between one and N, and N is a number of glycaemic risk measures in the plurality of glycaemic risk measures. The weight w applied to the ISF and each respective $c_i$ applied to a corresponding $x_i$ serves the additional purpose of providing the correct dimensions to the right hand side of the equation so that they match the dimensions of the fasting blood glucose target on the left hand side of the equation. That is, w not only weights ISF relative to $\Sigma_i^N c_i x_i$, but also provides the correct dimensions to ISF so that it matches the appropriate dimensions of FGL (e.g., mmol/L). Each $c_i$ serves as a weighting constant to weight the corresponding glycaemic risk measure $x_i$ relative to all other glycaemic measures as well as the ISF, and also provides the correct dimensions to the corresponding glycaemic risk measure $x_i$ (e.g., mmol/L). In some embodiments, w is unity (1), meaning that it only provides the correct dimensions to ISF. In some embodiments, w is some other value other than unity (1), meaning that weights ISF relative to $\Sigma_i^N c_i x_i$. In some embodiments, a given $c_i$ is unity meaning that it only provides the correct dimensions to the corresponding $x_i$. In some embodiments, a given $c_i$ is not unity meaning that it weights the corresponding $x_i$ relative to ISF and all other glycaemic measures. In some embodiments, N is a positive integer. In some embodiments N is 1, 2, 3, 4, 5, 6, 7, 8, 9, or 10. The FGL is depicted as a large X in panel A of FIGS. 14 and 15.

Block 432. Referring to block 432 of FIG. 4F, the method continues by communicating the basal insulin medicament titration schedule 238 (e.g., and in some embodiments the fasting blood glucose profile model 240 and/or the fasting blood glucose target 239) to: (i) the subject, (ii) an insulin pen 104 in one or more insulin pens charged with delivering the basal insulin medicament to the subject in accordance with the corresponding basal insulin medicament titration schedule (e.g., as dosage adjustment instructions) and/or (iii) a health care practitioner associated with the subject.

Referring to block 434 and as discussed above, in some embodiments, the method is repeated when the predicted fasting blood glucose profile is deemed not verified at a time in the second time course. For instance, referring to block 436, in some embodiments, a third dataset 242 representing all or a portion of the second time course is obtained. The third dataset comprises a plurality of fasting blood glucose values from the subject and, for each respective fasting glucose measurement 244 in the plurality of fasting glucose measurements, a time of measurement 246. In some embodiments, the fasting period is determined using the data from the first time course as discussed above in conjunction with FIGS. 9 and 10. For instance, it is determined that a particular time of day is the fasting period for the subject and this time of day is used to obtain the fasting glucose values in the second time course.

Referring to block 438, in some embodiments in accordance with block 436 the corresponding fasting blood glucose profile model is then verified against the third dataset by matching fasting blood glucose values in the third dataset against fasting blood glucose levels estimated by the corresponding fasting blood glucose profile model based upon the corresponding basal insulin medicament titration schedule. FIG. 14 illustrates. The fasting blood glucose profile model 240 is depicted as a dashed line in Panel A based upon the titration schedule in Panel B. The subject obtains fasting glucose measurements during the time course. If they do not match the predictions of the fasting blood glucose profile model, the fasting blood glucose profile model is deemed not verified, and the method further comprises adjusting the corresponding fasting blood glucose profile model and/or instructing the subject to repeat the data acquisition of the intensive measurement period and calculate a new basal insulin medicament titration schedule and a new corresponding fasting blood glucose profile model.

Referring to block 440, in other embodiments in accordance with block 436, a fourth dataset 302 that comprises a second plurality of insulin medicament records is obtained. Each respective insulin medicament record 304 in the second plurality of medicament records comprises: (i) a respective insulin medicament injection event 306 including an amount of insulin medicament injected 308 into the subject using a respective insulin pen of one or more insulin pens used by the subject, (ii) a corresponding timestamp 310 for the respective insulin medicament injection event, and (iii) a respective type of insulin medicament injected 312 into the subject from one of (a) the basal insulin medicament and (b) the bolus insulin medicament. In such embodiments, the corresponding fasting blood glucose profile model is verified against the third dataset by matching fasting blood glucose values in the third dataset against fasting blood glucose levels estimated by the corresponding fasting blood glucose profile model based upon the second plurality of medicament records in the fourth dataset. When the corresponding fasting blood glucose profile model is deemed not verified, the method further comprises adjusting the corresponding fasting blood glucose profile model. In this way, the fasting blood glucose profile model is rejected based upon the failure to predict fasting glucose measurements as a function of actual insulin medicament injection events rather than a titration schedule. In some embodiments this is favorable particularly when the subject fails to adhere to the titration schedule.

Example 1

Figure 8:
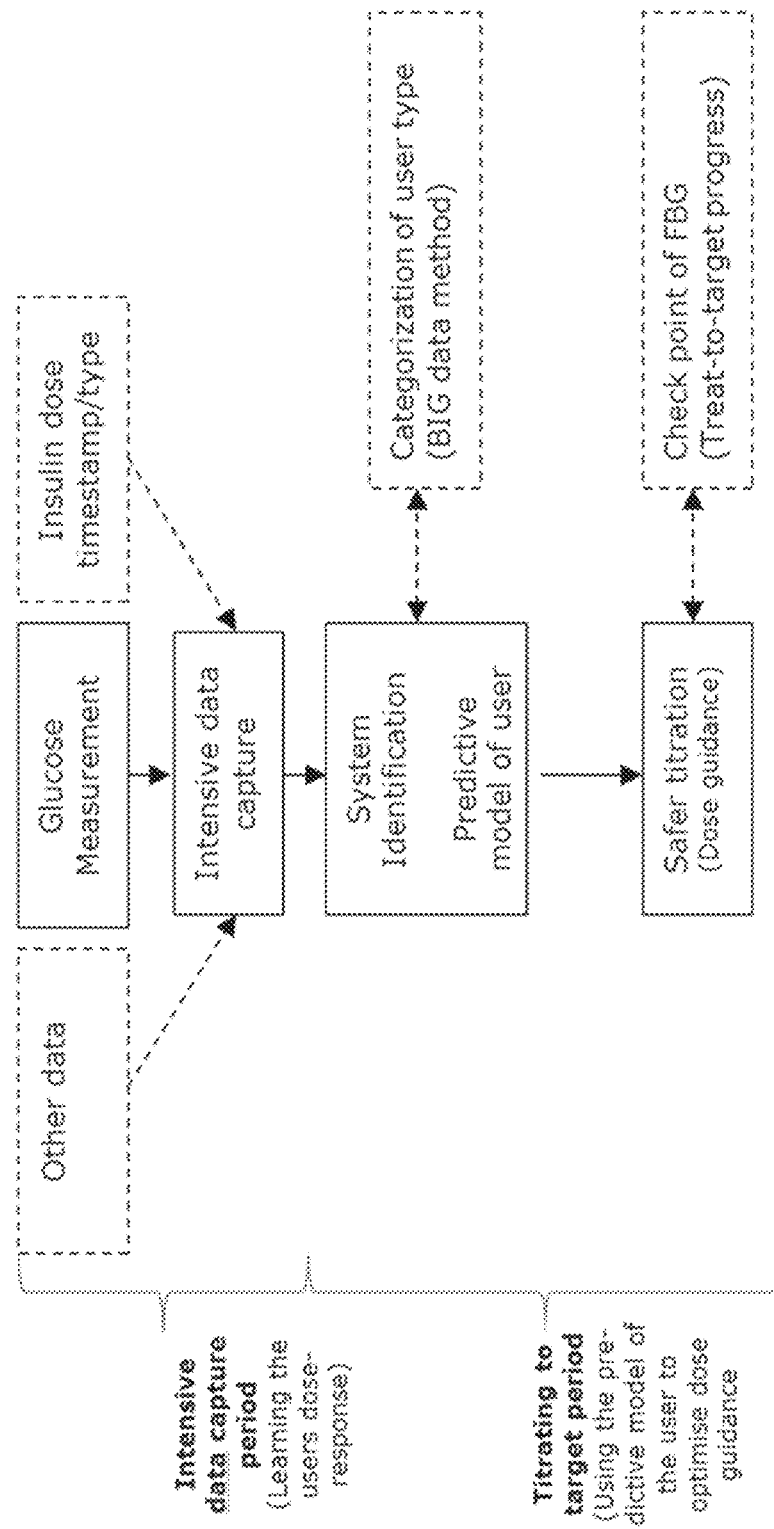
FIG. 8 illustrates a flow chart for determining a basal insulin medicament titration schedule identification for a subject, that optionally includes categorizing the subject, in accordance with an embodiment of the present disclosure.

Methods for obtaining a basal insulin medicament titration schedule have been disclosed. The following provides an example in accordance with FIG. 4 in reference to FIG. 8. A starter kit (e.g., basal titration adjustment module 204 of FIG. 2) captures an intensive amount of data relating to how the user responds to insulin. The data can be based on continuous glucose monitoring and insulin medicament dose size for a period of e.g. 14 days, as well as optional other data. After the first period (first time course) with intensive data capture, the starter kit system calculates and categorizes the patient's dose-response, variance in glucose, and risk of hypo/hyperglycaemia to create a treatment schedule comprising a robust predictive fasting blood glucose profile model and corresponding basal insulin medicament titration schedule. In some embodiments, the basal insulin medicament titration schedule is created using 'system identification methods' and 'categorization techniques' as discussed above in relation to blocks 426 and 428.

The treatment schedule also estimates how the fasting blood glucose of the subject will approach a target glucose level in the second time course after the intensive data acquisition of the first time course, and the subject can track the progress. The fasting blood glucose can be measured daily even less often; perhaps as little as once weekly during the second time course. This enables the subject to be guided during titration in a safer manner than any of the existing methods due to the use of a robust predictive model.

In some embodiments, the one or more processors 274 of the starter kit calculates a first glycaemic risk measure 234 and an insulin sensitivity factor 236 of the subject during the first time course, using data from a first dataset obtained from the continuous glucose monitor and a second dataset obtained from a connected insulin pen providing dose size and time stamps. In some embodiments, the method comprises using at least the first glycaemic risk measure and the insulin sensitivity factor of the subject and a fasting blood glucose profile model 240, based on a generic dose-response model of a person with diabetes, establishing a relation between the first glycaemic risk measure, the insulin sensitivity factor and (i) a corresponding basal insulin medicament titration schedule 238 for a second time course for the subject, wherein the second time course occurs subsequent to the first time course, and (ii) a corresponding fasting blood glucose profile model 240 over the second time course for the subject based on the corresponding basal insulin medicament titration schedule, wherein the corresponding fasting blood glucose profile model predicts the fasting blood glucose level of the subject based upon an amount of basal insulin medicament injected into the subject. Thereby the fasting blood glucose profile model, the first glyceamic risk measure and the insulin sensitivity factor can be used to obtain (i) a corresponding basal insulin medicament titration schedule 238 for a second time course for the subject, wherein the second time course occurs subsequent to the first time course, and (ii) a corresponding fasting blood glucose profile model 240 over the second time course for the subject based on the corresponding basal insulin medicament titration schedule, wherein the corresponding fasting blood glucose profile model predicts the fasting blood glucose level of the subject based upon an amount of basal insulin medicament injected into the subject.

In some embodiments, the fasting blood glucose profile model, based on a generic dose-response model of a person with diabetes is established based on the data obtained during the first time course, and used to predict the insulin medicament titration schedule, and the corresponding fasting blood glucose profile during the second time course.

The robustness of the prediction model is important when/if wrong data or poor adherence occurs. It is especially difficult for the existing titration algorithms/methods to handle non-fasting blood glucose measurements and missed injections. Advantageously, the disclosed systems and methods are able to detect most of these errors and correct them or minimize their influence on titration.

The predictive titration model will schedule the recommended daily dose, and it will optimize the dose advice based on the fasting blood glucose measurements during the titration period. A typical titration period can be between 2 to 8 weeks.

In some embodiments, the basal titration adjustment module 204 is based on a generic model of the dose-response model of a person with diabetes with a number of parameters (e.g. insulin sensitivity factor, etc.) and the system parameters are identified by standard system identification techniques, based on Model Predictive Control (MPC) techniques. As such, in some embodiments, the first step of the process is to analyze incoming data from patients from the first time course using a streaming clustering process in which an unsupervised clustering model, or a multi-factor clustering model incorporating robust regression techniques, continually refines patient population grouping boundaries until the individual patient can be fit into a subpopulation of patients having similar reactions to treatment. These serve as the basis of the treatment groups 316 illustrated in FIG. 3B. New subject will undergo a first time course of intensive data capture during which time the captured treatment data (fasting blood glucose, injection adherence, dose size, insulin sensitivity factor, blood glucose variance, glycemic risk, etc.) will be streamed into clustering model until sufficient confidence has been reached that the patient adequately fits into an identified subgroup. Once clustering has been completed (e.g., as described in blocks 426 and 428 of FIG. 4E) and the subject enters the second time course, individual patient treatment response within each group will be processed continually using a supervised machine learning decision model based on regression analysis, multiclass classification, or a combination of learning techniques. Each time the model is retrained on new patient treatment data during the secondary period, the ability of the model to predict each patient's reaction to treatment should improve, and the characterization of each treatment group 316 and their corresponding fasting blood glucose profile 240 and basal insulin medicament titration schedule 238 will improve. Frequency of self-administered treatment surveillance in the second time course in the form of fasting blood glucose measurements will be reduced over time (e.g. from once daily, to twice weekly, to once weekly, to bi-weekly) in accordance with the predictive model's continually-monitored level of success at predicting the patient's upcoming fasting blood glucose levels. The ongoing self-administered fasting blood glucose measurements can be seen as a calibration check for the predictive model.

In the event that the fasting blood glucose profile model 240 becomes unable to predict treatment reactions for a subject with sufficient accuracy or precision, whether due to subject behavioral changes or otherwise, a monitoring algorithm will indicate that frequency of self-administered fasting blood glucose profile model measurements should be increased, or in extreme cases that the patient should undergo a new starter period for reclassification.

An important element of the basal titration adjustment module 204 is that during the intensive data capture period of the first time course, the basal titration adjustment device 250 captures enough data to feed into a system identification process to generate a predictive model of the patient. The model will include one or more features selected from the groups consisting of i) dose response predictive model, ii) risk profile based on glucose variance data, iii) calculating the dose goal that will lower the lowest glucose data point into a treatment zone, and iv) inform the health care practitioner of the assessment on titration-plan, risk-profile, optimal timing for taking dose, optimal time for check-up at doctor.

The disclosed systems and method provide i) a model of how the subject will respond to treatment and/or schedule of how to titrate-to-target; 2) a risk indication to help the algorithm and health care practitioner to decide how to proceed; 3) a schedule of the minimum number of fasting blood glucose measurements needed to validate the prediction ongoing; 4) safe and robust dose guidance that is less sensitive to wrong data input in the secondary period of treatment; and display platforms for the titration schedule.

The outcome of the predictive insulin dose guidance system can be displayed in a number of ways (health care practitioner' computer, the Internet, a paper printout, short message service (SMS) message, directly in the basal titration adjustment module 204, etc.)

In view of the foregoing, a more intelligent approach to self-titration that enables an overall simpler and safer titration with less risk of hypoglycaemia is provided. The system improves safety due to better data and estimate of the patient's dose-response profile generated from an intensive period of data collection. The disclosed systems and methods minimize risk of erroneous blood glucose measurements altering the titration process. The disclosed systems and methods assure the subject that the titration guidance is correct by enabling them to verify that predicted fasting blood glucose is close to actual fasting blood glucose by measuring their daily fasting blood glucose level. The disclosed systems and methods minimize the number of daily treatment steps the user needs to perform to be adherent to the treatment plan. The disclosed systems and methods detect the lowest glucose level and variance for each day from day 0-14 and determine the permitted range in the fasting blood glucose that is optimal for the user. The disclosed systems and methods determines the optimal time to test the fasting blood glucose based on learnings from CGM-supported startup period of the first time course.

Further, the health care practitioner gets a comprehensive data package (user categorization) that enables the practitioner to decide optimal treatment regime, titration goal, and follow-up plan. The disclosed systems and methods enable the subject to learn how food, activity, and basal insulin affect the blood glucose.

LIST OF EMBODIMENTS

1. A device 250 for treatment of a subject, wherein the device comprises one or more processors 274 and a memory 192/290, the memory storing instructions that, when executed by the one or more processors, perform a method comprising:
   A) obtaining a first dataset 206, the first dataset comprising a plurality of autonomous glucose measurements of the subject over a first time course, and, for each respective glucose measurement 208 in the plurality of autonomous glucose measurements, a glucose measurement timestamp 210 representing when the respective measurement was made;
   B) obtaining a second dataset 212 associated with a standing insulin regimen 224 for the subject over the first time course, wherein
      the second dataset comprises a first plurality of insulin medicament records, and
      each respective insulin medicament record 214 in the first plurality of insulin medicament records comprises: (i) a respective insulin medicament injection event 216 including an amount of insulin medicament injected 218 into the subject using a respective insulin pen 104 of one or more insulin pens used by the subject, (ii) a corresponding insulin medicament injection event timestamp 220 for the respective insulin medicament injection event, and (iii) a respective type of insulin medicament 222 injected into the subject from one of (a) a basal insulin medicament and (b) a bolus insulin medicament;
   C) using the first dataset and the second dataset to calculate a first glycaemic risk measure 234 and an insulin sensitivity factor 236 of the subject during the first time course;
   D) using at least the first glycaemic risk measure and the insulin sensitivity factor of the subject to obtain
      (i) a corresponding basal insulin medicament titration schedule 238 for a second time course for the subject, wherein the second time course occurs subsequent to the first time course, and
      (ii) a corresponding fasting blood glucose profile model 240 over the second time course for the subject based on the corresponding basal insulin medicament titration schedule, wherein the corresponding fasting blood glucose profile model predicts the fasting blood glucose level of the subject based upon an amount of basal insulin medicament injected into the subject; and
   E) communicating the corresponding basal insulin medicament titration schedule to (i) the subject, (ii) an insulin pen in the one or more insulin pens charged with delivering the basal insulin medicament to the subject in accordance with the corresponding basal insulin medicament titration schedule, and/or (iii) a health care practitioner associated with the subject.

2. The device of embodiment 1, wherein the method further comprises:
   F) obtaining a third dataset (242) representing all or a portion of the second time course, wherein the third dataset comprises a plurality of fasting blood glucose values from the subject and, for each respective fasting glucose measurement (244) in the plurality of fasting glucose measurements, a time of measurement (246); and
   G) verifying the corresponding fasting blood glucose profile model against the third dataset by matching fasting blood glucose values in the third dataset against fasting blood glucose levels estimated by the corresponding fasting blood glucose profile model based upon the corresponding basal insulin medicament titration schedule, wherein, when the corresponding fasting blood glucose profile model is deemed not verified, the method further comprises adjusting the corresponding fasting blood glucose profile model.

3. The device of embodiment 1, the method further comprising:
   F) obtaining a third dataset (242) representing all or a portion of the second time course, wherein the third dataset comprises a plurality of fasting blood glucose values from the subject and, for each respective fasting glucose measurement (244) in the plurality of fasting glucose measurements, a time of measurement (246); and
   G) obtaining a fourth dataset (302) that comprises a second plurality of insulin medicament records, wherein, each respective insulin medicament record (304) in the second plurality of medicament records comprises: (i) a respective insulin medicament injection event (306) including an amount of insulin medicament injected (308) into the subject using a respective insulin pen of one or more insulin pens used by the subject, (ii) a corresponding timestamp (310) for the respective insulin medicament injection event, and (iii) a respective type of insulin medicament injected (312) into the subject from one of (a) the basal insulin medicament and (b) the bolus insulin medicament; and
   H) verifying the corresponding fasting blood glucose profile model against the third dataset by matching fasting blood glucose values in the third dataset against fasting blood glucose levels estimated by the corresponding fasting blood glucose profile model based upon the second plurality of medicament records in the fourth dataset, wherein, when the corresponding fasting blood glucose profile model is deemed not verified, the method further comprises adjusting the corresponding fasting blood glucose profile model.

4. The device of embodiment 1, wherein
   the using at least the first glycaemic risk measure and the insulin sensitivity factor of the subject in step D) comprises identifying a first treatment group (316) in a plurality of treatment groups, wherein
   each respective treatment group in the plurality of treatment groups is independently associated with a corresponding supervised classifier (318) in a plurality of supervised classifiers, and
   the supervised classifier of the first treatment group is used to compute the corresponding fasting blood glucose profile model and the corresponding basal insulin medicament titration schedule for the second time course for the subject, thereby obtaining the corresponding basal insulin medicament titration schedule and the corresponding fasting blood glucose profile model.

5. The device of embodiment 4, wherein the identifying the first treatment group in the plurality of treatment groups comprises co-clustering a vector of metrics (320) obtained from at least the first dataset and the second dataset, against each treatment group in the plurality of treatment groups thereby obtaining a respective distance score against each treatment group in the plurality of treatment groups, wherein
the vector of metrics comprises the first glycaemic risk measure and the insulin sensitivity factor of the subject, and
the first treatment group is identified from among the plurality of treatment groups when the distance score for the first treatment group satisfies a confidence threshold.

6. The device of any one of embodiments 1-5, wherein the using the first dataset and the second dataset to calculate the first glycaemic risk measure of the subject during the first time course comprises determining:
(i) a total glucose level variability observed across the plurality of autonomous glucose measurements,
(ii) a fasting glucose level calculated from the plurality of autonomous glucose measurements,
(iii) a minimum glucose measurement observed in the plurality of autonomous glucose measurements,
(iv) a maximum glucose measurement observed in the plurality of autonomous glucose measurements,
(v) a rate of change in the insulin sensitivity factor calculated using the plurality of autonomous glucose measurements and the second dataset,
(vi) a basal adherence score over the first time course that is computed by dividing (a) a number of insulin medicament injection events that were taken by the subject when dictated by the standing insulin regimen by (b) a total number of basal insulin medicament injection events dictated by the standing insulin regimen in the first time course,
(vii) a percentage of the time glucose levels of the subject are above a first target range across the plurality of autonomous glucose measurements,
(viii) a percentage of the time glucose level of the subject are below the first target range across the plurality of autonomous glucose measurements,
(ix) a percentage of the time the glucose level of the subject is outside the first target range across the plurality of autonomous glucose measurements, or
(x) a measure of spread of the plurality of autonomous glucose measurements.

7. The device of embodiment 6, wherein the first glycaemic risk measure comprises the fasting glucose level calculated from the plurality of autonomous glucose measurements, wherein the fasting glucose level is computed by computing a moving period of variance $\sigma_k^2$ across the plurality of autonomous glucose measurements, wherein:

$$\sigma_k^2 = \frac{1}{M} \sum_{i=k-M+1}^{k} (G_i - \overline{G})^2$$

wherein,
$G_i$ is the $i^{th}$ autonomous glucose measurement in a portion k of the plurality of autonomous glucose measurements,
M is a number of autonomous glucose measurements in the plurality of glucose measurements and represents a respective contiguous predetermined time span within the first time course,
$\overline{G}$ is the mean of the autonomous glucose measurements selected from the plurality of autonomous glucose measurements, and k is within the respective contiguous predetermined time span;
associating a fasting period in the first time course with a respective contiguous predetermined time span exhibiting a minimum variance $$\min_k \sigma_k^2;$$

and
computing the fasting glucose level using autonomous glucose measurements in the plurality of autonomous glucose measurements in the fasting period.

8. The device of embodiment 7, wherein the first fasting glucose level comprises:
(i) the minimum autonomous glucose measurement in the autonomous glucose measurements in the fasting period,
(ii) a measure of central tendency across the autonomous glucose measurements in the fasting period,
(iii) a range exhibited by the autonomous glucose measurements in the fasting period,
(iv) an interquartile range across the autonomous glucose measurements in the fasting period,
(v) a variance across the autonomous glucose measurements in the fasting period,
(vi) an average squared difference across the autonomous glucose measurements in the fasting period from the mean (μ) of the autonomous glucose measurements in the fasting period ($\sigma^2$) computed as:

$$\sigma^2 = \frac{\sum_i^P (m_i - \mu)^2}{P}$$

wherein,
$m_i$ is the $i^{th}$ autonomous glucose measurement in the fasting period, and
P is a number of autonomous glucose measurements in the fasting period, and
(vii) a standard deviation of the autonomous glucose measurements across the autonomous glucose measurements in the fasting period computed as $\sqrt{\sigma^2}$.

9. The device of any one of embodiments 1-8, the method further comprising:
obtaining a fifth dataset (322), wherein the fifth dataset comprises auxiliary data (324) associated with the subject in the first time course, wherein the auxiliary data comprises one or more of energy exerted by the subject, subject weight, subject age, and subject meal activity during the first time course; and
the fifth dataset is used in step D) in conjunction with the first glycaemic risk measure and the insulin sensitivity factor of the subject to obtain the corresponding basal insulin medicament titration schedule and the corresponding fasting blood glucose profile model over the second time course.

10. The device of any one of embodiments 1-9, wherein the standing insulin regimen for the subject over the first time course specifies a plurality of epochs (n) within the first time course, and a different daily total basal insulin medicament dosage for each respective epoch in the plurality of epochs, and the insulin sensitivity factor (ISF) is calculated by:

$$ISF = \left(\frac{1}{\left(\frac{n!}{(n-2)!}\right)}\right) \sum_{n, i \neq j}^{\frac{n!}{(n-2)!}} \frac{\Delta FG_{i,j}}{\Delta U_{i,j}}$$

wherein,
 i is a first index into the plurality of epochs,
 j is a second index into the plurality of epochs,
 $\Delta FG_{i,j}$ is the difference in average fasting glucose level of the subject between epoch i and epoch j, and
 $\Delta U_{i,j}$ is the difference in daily insulin dose size of the subject between epoch i and epoch j as determined by the standing insulin regimen or the second dataset.

11. The device of any one of embodiments 1-10, wherein the method is repeated when the predicted fasting blood glucose profile is deemed not verified at a time in the second time course.

12. The device of embodiment 2, wherein successive measurements in the plurality of autonomous glucose measurements in the second dataset are taken at an interval rate of one day, two days, three days, four days, five days, six days, or seven days.

13. The device of any one of embodiments 1-12, wherein the corresponding basal insulin medicament titration schedule has a fasting blood glucose target (FGL) (239) that is calculated as:

$$FGL = (w * ISF) + \Sigma_i^N c_i x_i$$

wherein,
 w is a scaling weight,
 ISF is the insulin sensitivity factor of the subject calculated from the first and second datasets over the first time course,
 $c_i$ is an $i^{th}$ weighting constant applied to an $x_i^{th}$ glycaemic risk measure, wherein the $x_i^{th}$ glycaemic risk measure is in a plurality of glycaemic risk measures that includes the first glycaemic risk measure,
 i is an index between one and N; and
 N is a number of glycaemic risk measures in the plurality of glycaemic risk measures.

14. The device of any one of embodiments 1-13, wherein successive measurements in the plurality of autonomous glucose measurements in the second dataset are taken from a measurement apparatus worn by the subject at an interval rate of 5 minutes or less, 3 minutes or less, or 1 minute or less.

15. The device of any on of embodiments 1-14, wherein the second data set is obtained from a respective insulin pen (104) of one or more connected insulin pens used by the subject, and wherein a corresponding insulin medicament injection event timestamp (220) is automatically generated by the respective insulin pen upon occurrence of the respective insulin medicament injection event.

16. A method comprising:
 at a computer system comprising one or more processors and a memory, using the computer system to perform a method comprising:
 A) obtaining a first dataset for a subject, the first dataset comprising a plurality of autonomous glucose measurements of the subject over a first time course, and, for each respective glucose measurement in the plurality of autonomous glucose measurements, a glucose measurement timestamp representing when the respective measurement was made;
 B) obtaining a second dataset associated with a standing insulin regimen for the subject over the first time course, wherein
   the second dataset comprises a first plurality of insulin medicament records, and
   each respective insulin medicament record in the first plurality of medicament records comprises: (i) a respective insulin medicament injection event including an amount of insulin medicament injected into the subject using a respective insulin pen of one or more insulin pens used by the subject, (ii) a corresponding insulin medicament injection event timestamp for the respective insulin medicament injection event, and (iii) a respective type of insulin medicament injected into the subject from one of (a) a basal insulin medicament and (b) a bolus insulin medicament;
 C) using the first dataset and the second dataset to calculate a glycaemic risk measure and an insulin sensitivity factor of the subject during the first time course;
 D) using at least the glycaemic risk measure and the insulin sensitivity factor of the subject to obtain
   (i) a corresponding basal insulin medicament titration schedule for a second time course, wherein the second time course occurs subsequent to the first time course, and
   (ii) a corresponding fasting blood glucose profile model over the second time course for the subject based on the corresponding basal insulin medicament titration schedule, wherein the fasting blood glucose profile model predicts the fasting blood glucose level of the subject based upon an amount of basal insulin medicament specified by the fasting blood glucose profile model; and
 E) communicating the corresponding basal insulin medicament titration schedule to (i) the subject, (ii) an insulin pen in the one or more insulin pens charged with delivering the basal insulin medicament to the subject in accordance with the corresponding basal insulin medicament titration schedule, and/or (iii) a health care practitioner associated with the subject.

17. A computer program comprising instructions that, when executed by a computer having one or more processors and a memory, perform the method of embodiment 16.

18. A computer-readable data carrier having stored thereon the computer program according to embodiment 17.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIGS. 1, 2, 3, 5 and/or described in FIG. 4. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

The invention claimed is:

1. A device for treatment of a subject, wherein the device comprises one or more processors and a memory, the memory storing instructions that, when executed by the one or more processors, perform a method comprising:
   A) obtaining a first dataset, the first dataset comprising a plurality of autonomous glucose measurements of the subject over a first time course, and, for each respective glucose measurement in the plurality of autonomous glucose measurements, a glucose measurement timestamp representing when the respective measurement was made;
   B) obtaining a second dataset associated with a standing insulin regimen for the subject over the first time course, wherein the second dataset comprises a first plurality of insulin medicament records, and each respective insulin medicament record in the first plurality of insulin medicament records comprises: (i) a respective insulin medicament injection event including an amount of insulin medicament injected into the subject using a respective insulin pen of one or more insulin pens used by the subject, (ii) a corresponding insulin medicament injection event timestamp for the respective insulin medicament injection event, and (iii) a respective type of insulin medicament injected into the subject from one of (a) a basal insulin medicament and (b) a bolus insulin medicament;
   C) using the first dataset to calculate a first glycaemic risk measure, and using the first dataset and the second dataset to calculate an insulin sensitivity factor of the subject during the first time course;
   D) using at least the first glycaemic risk measure and the insulin sensitivity factor of the subject to obtain
      (i) a corresponding basal insulin medicament titration schedule for a second time course for the subject, the basal insulin medicament titration schedule comprising a plurality of basal insulin medicament values defined over a period of time, each of the plurality of basal insulin medicament values being different from one another, wherein the second time course occurs subsequent to the first time course, and
      (ii) a corresponding fasting blood glucose profile model over the second time course for the subject based on the corresponding basal insulin medicament titration schedule, wherein the corresponding fasting blood glucose profile model predicts the fasting blood glucose level of the subject based upon an amount of basal insulin medicament injected into the subject, wherein the using at least the first glycaemic risk measure and the insulin sensitivity factor of the subject to obtain
      (i) the corresponding basal insulin medicament titration schedule and (ii) the corresponding fasting blood glucose profile model comprises iteratively training and retraining, based on a plurality of sets of new patient treatment data provided from the subject at a plurality of time instances during the second time course, a supervised machine learning decision model, and generating, with said supervised machine learning decision model and after training said supervised machine learning decision model, the corresponding basal insulin medicament titration schedule and the corresponding fasting blood glucose profile model; and
   E) communicating the corresponding basal insulin medicament titration schedule to:
      (i) the subject,
      (ii) an insulin pen in the one or more insulin pens charged with delivering the basal insulin medicament to the subject in accordance with the corresponding basal insulin medicament titration schedule, and/or
      (iii) a health care practitioner associated with the subject.

2. The device of claim 1, wherein the method further comprises:
   F) obtaining a third dataset representing all or a portion of the second time course, wherein the third dataset comprises a plurality of fasting blood glucose values from the subject and, for each respective fasting glucose measurement in the plurality of fasting glucose measurements, a time of measurement; and
   G) verifying the corresponding fasting blood glucose profile model against the third dataset by matching fasting blood glucose values in the third dataset against fasting blood glucose levels estimated by the corresponding fasting blood glucose profile model based upon the corresponding basal insulin medicament titration schedule, wherein, when the corresponding fasting blood glucose profile model is deemed not verified, the method further comprises adjusting the corresponding fasting blood glucose profile model.

3. The device of claim 1, the method further comprising:
   F) obtaining a third dataset representing all or a portion of the second time course, wherein the third dataset comprises a plurality of fasting blood glucose values from the subject and, for each respective fasting glucose measurement in the plurality of fasting glucose measurements, a time of measurement; and
   G) obtaining a fourth dataset that comprises a second plurality of insulin medicament records, wherein, each respective insulin medicament record in the second plurality of medicament records comprises: (i) a respective insulin medicament injection event including an amount of insulin medicament injected into the subject using a respective insulin pen of one or more insulin pens used by the subject, (ii) a corresponding timestamp for the respective insulin medicament injection event, and (iii) a respective type of insulin medicament injected into the subject from one of (a) the basal insulin medicament and (b) the bolus insulin medicament; and
   H) verifying the corresponding fasting blood glucose profile model against the third dataset by matching fasting blood glucose values in the third dataset against fasting blood glucose levels estimated by the corresponding fasting blood glucose profile model based upon the second plurality of medicament records in the fourth dataset, wherein, whoa the corresponding fasting blood glucose profile model is deemed not verified, the method further comprises adjusting the corresponding fasting blood glucose profile model.

4. The device of claim 1, wherein
the using at least the first glycaemic risk measure and the insulin sensitivity factor of the subject in step D) comprises identifying a first treatment group in a plurality of treatment groups,
wherein each respective treatment group in the plurality of treatment groups is independently associated with a corresponding supervised classifier in a plurality of supervised classifiers, and
the supervised classifier of the first treatment group is used to compute the corresponding fasting blood glucose profile model and the corresponding basal insulin medicament titration schedule for the second time course for the subject, thereby obtaining the corresponding basal insulin medicament titration schedule and the corresponding fasting blood glucose profile model.

5. The device of claim 4, wherein the identifying the first treatment group in the plurality of treatment groups comprises co-clustering a vector of metrics obtained from at least the first dataset and the second dataset, against each treatment group in the plurality of treatment groups thereby obtaining a respective distance score against each treatment group in the plurality of treatment groups,
wherein the vector of metrics comprises the first glycaemic risk measure and the insulin sensitivity factor of the subject, and
the first treatment group is identified from among the plurality of treatment groups when the distance score for the first treatment group satisfies a confidence threshold.

6. The device of claim 1, wherein the using the first dataset and the second dataset to calculate the first glycaemic risk measure of the subject during the first time course comprises determining:
(i) a total glucose level variability observed across the plurality of autonomous glucose measurements,
(ii) a fasting glucose level calculated from the plurality of autonomous glucose measurements,
(iii) a minimum glucose measurement observed in the plurality of autonomous glucose measurements,
(iv) a maximum glucose measurement observed in the plurality of autonomous glucose measurements,
(v) a rate of change in the insulin sensitivity factor calculated using the plurality of autonomous glucose measurements and the second dataset,
(vi) a basal adherence score over the first time course that is computed by dividing (a) a number of insulin medicament injection events that were taken by the subject when dictated by the standing insulin regimen by (b) a total number of basal insulin medicament injection events dictated by the standing insulin regimen in the first time course,
(vii) a percentage of the time that glucose levels of the subject are above a first target range across the plurality of autonomous glucose measurements,
(viii) a percentage of the time that glucose levels of the subject are below the first target range across the plurality of autonomous glucose measurements,
(ix) a percentage of the time the glucose level of the subject is outside the first target range across the plurality of autonomous glucose measurements, or
(x) a measure of spread of the plurality of autonomous glucose measurements.

7. The device of claim. 6, wherein the first glycaemic risk measure comprises the fasting glucose level calculated from the plurality of autonomous glucose measurements, wherein the fasting glucose level is computed by computing a moving period of variance $\sigma_k^2$ across the plurality of autonomous glucose measurements, wherein:

$$\sigma_k^2 = \frac{1}{M} \sum_{i=k-M+1}^{k} (G_i - \overline{G})^2$$

wherein,
$G_i$ is the $i^{th}$ autonomous glucose measurement in a portion k of the plurality of autonomous glucose measurements,
M is a number of autonomous glucose measurements in the plurality of glucose measurements and represents a respective contiguous predetermined time span within the first time course,
$\overline{G}$ is the mean of the autonomous glucose measurements selected from the plurality of autonomous glucose measurements, and
k is within the respective contiguous predetermined time span;
associating a fasting period in the first time course with a respective contiguous predetermined time span exhibiting a minimum variance $$\min_{k} \sigma_k^2;$$

and
computing the fasting glucose level using autonomous glucose measurements in the plurality of autonomous glucose measurements in the fasting period.

8. The device of claim 7, wherein the first fasting glucose level is determined based on:
(i) the minimum autonomous glucose measurement in the autonomous glucose measurements in the fasting period,
(ii) a measure of central tendency across the autonomous glucose measurements in the fasting period,
(iii) a range exhibited by the autonomous glucose measurements in the fasting period,
(iv) an interquartile range across the autonomous glucose measurements in the fasting period,
(v) a variance across the autonomous glucose measurements in the fasting period,
(vi) an average squared difference across the autonomous glucose measurements in the fasting period from the mean ($\mu$) of the autonomous glucose measurements in the fasting period ($\sigma^2$) computed as:

$$\sigma^2 = \frac{\sum_{i}^{P} (m_i - \mu)^2}{P}$$

wherein,
$m_i$ is the $i^{th}$ autonomous glucose measurement in the fasting period, and
P is a number of autonomous glucose measurements in the fasting period, and (vii) a standard deviation of the autonomous glucose measurements across the autonomous glucose measurements in the fasting period computed as $\sqrt{\sigma^2}$.

9. The device of claim 1, the method further comprising:
obtaining a fifth dataset, wherein the fifth dataset comprises auxiliary data associated with the subject in the first time course, wherein the auxiliary data comprises one or more of energy exerted by the subject, subject weight, subject age, and subject meal activity during the first time course; and
the fifth dataset is used in step D) in conjunction with the first glycaemic risk measure and the insulin sensitivity factor of the subject to obtain the corresponding basal insulin medicament titration schedule and the corresponding fasting blood glucose profile model over the second time course.

10. The device of claim 1, wherein the standing insulin regimen for the subject over the first time course specifies a plurality of epochs (n) within the first time course, and a different daily total basal insulin medicament dosage for each respective epoch in the plurality of epochs, and
the insulin sensitivity factor (ISF) is calculated by:

$$ISF = \left(\frac{1}{\left(\frac{n!}{(n-2)!}\right)}\right) \sum_{n,i \neq j}^{\frac{n!}{(n-2)!}} \frac{\Delta FG_{i,j}}{\Delta U_{i,j}}$$

wherein,
i is a first index into the plurality of epochs,
j is a second index into the plurality of epochs,
$\Delta FG_{i,j}$ is the difference in average fasting glucose level of the subject between epoch i and epoch j, and
$\Delta U_{i,j}$ is the difference in daily insulin dose size of the subject between epoch i and epoch j as determined by the standing insulin regimen or the second dataset.

11. The device of claim 1, wherein the method is repeated when the predicted fasting blood glucose profile is deemed not verified at a time in the second time course.

12. The device of claim 2, wherein successive measurements in the plurality of autonomous glucose measurements in the second dataset are taken at an interval rate of one day, two days, three days, four days, five days, six days, or seven days.

13. The device of claim 1, wherein the corresponding basal insulin medicament titration schedule has a fasting blood glucose target (FGL) that is calculated as:

$$FGL = (w * ISF) + \Sigma_i^N c_i x_i$$

wherein,
w is a scaling weight,
ISF is the insulin sensitivity factor of the subject calculated from the first and second datasets over the first time course,
$c_i$ is an $i^{th}$ weighting constant applied to an $x_i^{th}$ glycaemic risk measure, wherein the $x_i^{th}$ glycaemic risk measure is in a plurality of glycaemic risk measures that includes the first glycaemic risk measure,
i is an index between one and N; and
N is a number of glycaemic risk measures in the plurality of glycaemic risk measures.

14. The device of claim 1, wherein successive measurements in the plurality of autonomous glucose measurements in the second dataset are taken from a measurement apparatus worn by the subject at an interval rate of 5 minutes or less, 3 minutes or less, or 1 minute or less.

15. The device of claim 1, wherein the second data set is obtained from a respective insulin pen of one or more connected insulin pens used by the subject, and wherein a corresponding insulin medicament injection event timestamp is automatically generated by the respective insulin pen upon occurrence of the respective insulin medicament injection event.

16. A method comprising:
at a computer system comprising one or more processors and a memory, using the computer system to perform steps comprising:
A) obtaining a first dataset for a subject, the first dataset comprising a plurality of autonomous glucose measurements of the subject over a first time course, and, for each respective glucose measurement in the plurality of autonomous glucose measurements, a glucose measurement timestamp representing when the respective measurement was made;
B) obtaining a second dataset associated with a standing insulin regimen for the subject over the first time course, wherein the second dataset comprises a first plurality of insulin medicament records, and each respective insulin medicament record in the first plurality of medicament records comprises:
(i) a respective insulin medicament injection event including an amount of insulin medicament injected into the subject using a respective insulin pen of one or more insulin pens used by the subject,
(ii) a corresponding insulin medicament injection event timestamp for the respective insulin medicament injection event, and
(iii) a respective type of insulin medicament injected into the subject from one of (a) a basal insulin medicament and (b) a bolus insulin medicament;
C) using the first dataset and the second dataset to calculate a glycaemic risk measure and an insulin sensitivity factor of the subject during the first time course;
D) using at least the glycaemic risk measure and the insulin sensitivity factor of the subject to obtain
(i) a corresponding basal insulin medicament titration schedule for a second time course, wherein the second time course occurs subsequent to the first time course, the basal insulin medicament titration schedule comprising a plurality of basal insulin medicament values defined over a period of time, each of the plurality of basal insulin medicament values being different from one another, and
(ii) a corresponding fasting blood glucose profile model over the second time course for the subject based on the corresponding basal insulin medicament titration schedule, wherein the fasting blood glucose profile model predicts the fasting blood glucose level of the subject based upon an amount of basal insulin medicament specified by the fasting blood glucose profile model,
wherein the using at least the first glycaemic risk measure and the insulin sensitivity factor of the subject to obtain (i) the corresponding basal insulin medicament titration schedule and (ii) the corresponding fasting blood glucose profile model comprises iteratively training and retraining, based on a plurality of sets of new patient treatment data provided from the subject at a plurality of time instances during the second time course, a supervised machine learning decision model, and generating, with said supervised machine learning decision model and after training said supervised machine learning decision model, the corresponding basal insulin medicament titration schedule and the corresponding fasting blood glucose profile model; and (E) communicating the corresponding basal insulin medicament titration schedule to (i) the subject, (ii) an insulin pen in the one or more insulin pens charged with delivering the basal insulin medicament to the subject in accordance with the corresponding basal insulin medicament titration schedule, and/or (iii) a health care practitioner associated with the subject.

17. A non-transitory computer-readable medium comprising instructions that, when executed by the computer system having the one or more processors and the memory of claim 16, perform the method of claim 16.

18. The device of claim 1, wherein the super supervised machine learning decision model is based on regression analysis, multiclass classification, or a combination thereof.

* * * * *

UNITED STATES PATENT AND TRADEMARK OFFICE
CERTIFICATE OF CORRECTION

| | |
|---|---|
| PATENT NO. | : 11,282,598 B2 |
| APPLICATION NO. | : 16/327502 |
| DATED | : March 22, 2022 |
| INVENTOR(S) | : Brad Van Orden et al. |

It is certified that error appears in the above-identified patent and that said Letters Patent is hereby corrected as shown below:

In the Claims

At Column 47, Claim number 18, please replace Line 17 with the following:
"The device of claim 1, wherein the supervised"

Signed and Sealed this
Eighteenth Day of October, 2022

Katherine Kelly Vidal
*Director of the United States Patent and Trademark Office*